US012714648B2

(12) United States Patent
Hadad et al.

(10) Patent No.: US 12,714,648 B2
(45) Date of Patent: Aug. 25, 2026

(54) CLOSED SYSTEM FOR STERILE DRUG PREPARATION AND ADMINISTRATION

(71) Applicant: Rambam MedTech Ltd., Haifa (IL)

(72) Inventors: Salim Hadad, Haifa (IL); Zvi Lefel, Haifa (IL)

(73) Assignee: RAMBAM MEDTECH LTD., Haifa (IL)

( * ) Notice: Subject to any disclaimer, the term of this patent is extended or adjusted under 35 U.S.C. 154(b) by 406 days.

(21) Appl. No.: 18/292,616

(22) PCT Filed: Aug. 22, 2022

(86) PCT No.: PCT/IL2022/050914
§ 371 (c)(1),
(2) Date: Jan. 26, 2024

(87) PCT Pub. No.: WO2023/031910
PCT Pub. Date: Mar. 9, 2023

(65) Prior Publication Data

US 2024/0366476 A1 Nov. 7, 2024

Related U.S. Application Data

(60) Provisional application No. 63/239,998, filed on Sep. 2, 2021.

(51) Int. Cl.
*A61J 1/20* (2006.01)
*A61M 5/14* (2006.01)

(52) U.S. Cl.
CPC ........... *A61J 1/2089* (2013.01); *A61J 1/2013* (2015.05); *A61J 1/2062* (2015.05); *A61M 5/1414* (2013.01)

(58) Field of Classification Search
CPC ........... A61J 1/20; A61J 1/2089; A61J 1/2096
See application file for complete search history.

(56) References Cited

U.S. PATENT DOCUMENTS 4,410,321 A * 10/1983 Pearson ................ A61J 1/2089 604/82
4,606,734 A 8/1986 Larkin et al.
(Continued)

FOREIGN PATENT DOCUMENTS

AU 2013200393 2/2013
CN 105267037 1/2016
(Continued)

OTHER PUBLICATIONS

Tevadaptor® Spike Port Adaptor—Technical Datasheet Feb. 2018.
(Continued)

*Primary Examiner* — David P. Olynick
(74) *Attorney, Agent, or Firm* — Sughrue Mion, PLLC

(57) ABSTRACT

A sterile closed system (20, 120) is provided that includes an airtight enclosure (40), an infusion-bag receptacle (44), medication-preparation tubing (48), one or more medication-preparation-tubing valves (50, 250), and an infusion-bag seal (46), which is configured to make an airtight seal with respective external surfaces of a medication port (36) and an IV tubing port (34) of an infusion bag (32). A medication-vial port (53) is configured to be sealingly coupled to a medication vial (30). The sterile closed system (20, 120) is configured such that a medication-port-interface needle (60), disposed within an enclosure interior (42) of the airtight enclosure (40), is sealingly couplable to the medication port (36) of the infusion bag (32), and an IV-tubing-port-interface spike (64), disposed within the enclosure interior (42), is sealingly couplable to the IV tubing port (34) of the infusion bag (32) without breaking the airtight seal between the infusion-bag seal (46) and the respective external surfaces of the medication port (36) and the IV tubing port (34) of the infusion bag (32). Other embodiments are also described.

20 Claims, 18 Drawing Sheets

(56) References Cited

U.S. PATENT DOCUMENTS

| | | | | |
|---|---|---|---|---|
| 4,610,684 A * | 9/1986 | Knox | A61J 1/2093 604/416 |
| 4,768,568 A | 9/1988 | Fournier et al. | |
| 5,122,116 A | 6/1992 | Kriesel et al. | |
| 5,328,464 A | 7/1994 | Kriesel et al. | |
| 5,385,545 A | 1/1995 | Kriesel et al. | |
| 5,490,848 A | 2/1996 | Finley et al. | |
| 5,583,052 A | 12/1996 | Portnoff et al. | |
| 5,817,083 A | 10/1998 | Shemesh et al. | |
| 5,944,709 A * | 8/1999 | Barney | A61J 1/10 604/416 |
| 6,478,771 B1 | 11/2002 | Lavi et al. | |
| 7,744,581 B2 | 6/2010 | Wallén et al. | |
| 7,896,849 B2 | 3/2011 | Delay | |
| 7,998,106 B2 | 8/2011 | Thorne, Jr. et al. | |
| 8,151,835 B2 | 4/2012 | Khan et al. | |
| 8,506,548 B2 | 8/2013 | Okiyama | |
| 8,562,583 B2 | 10/2013 | Akerlund et al. | |
| 8,905,994 B1 | 12/2014 | Lev et al. | |
| 9,039,672 B2 | 5/2015 | Wallen et al. | |
| 9,221,045 B2 | 12/2015 | Yoshida et al. | |
| 9,345,643 B2 | 5/2016 | Okiyama | |
| 9,433,726 B2 | 9/2016 | Creaturo | |
| 9,539,241 B2 | 1/2017 | Timm | |
| 9,775,946 B2 * | 10/2017 | McNall, III | A61J 1/2093 |
| 9,795,536 B2 | 10/2017 | Lev et al. | |
| 9,999,570 B2 | 6/2018 | Sanders et al. | |
| 10,010,481 B2 * | 7/2018 | Gobbi Frattini | A61J 1/2089 |
| 10,406,072 B2 | 9/2019 | Chhikara et al. | |
| 10,406,279 B2 | 9/2019 | Mcnall, III et al. | |
| 10,420,927 B2 | 9/2019 | Fangrow | |
| 10,806,668 B2 | 10/2020 | Akerlund et al. | |
| 11,338,082 B2 * | 5/2022 | McNall, III | A61J 1/2024 |
| 2003/0199847 A1 | 10/2003 | Akerlund et al. | |
| 2006/0049209 A1 * | 3/2006 | Baker | A61J 1/2089 222/252 |
| 2008/0051937 A1 | 2/2008 | Khan et al. | |
| 2009/0093757 A1 | 4/2009 | Tennican | |
| 2009/0145509 A1 | 6/2009 | Baker et al. | |
| 2011/0034870 A1 | 2/2011 | Glejboel et al. | |
| 2012/0089088 A1 * | 4/2012 | Foshee | A61J 1/2089 53/425 |
| 2013/0225903 A1 * | 8/2013 | Franci | A61N 5/1007 600/4 |
| 2013/0281964 A1 | 10/2013 | Kugelmann et al. | |
| 2019/0298612 A1 | 10/2019 | Gobbi Frattini | |

FOREIGN PATENT DOCUMENTS

| | | |
|---|---|---|
| CN | 104830682 | 8/2017 |
| JP | 2987597 | 12/1999 |
| WO | 2011/027207 | 3/2011 |

OTHER PUBLICATIONS

Stoker Oct. 2009 Preventing_injuries_from_glass_ampoule_shards.

Starr Systems Products—Disposable Ampoule Breaker downloaded Jul. 26, 2021.

JMS NeoShield Brochure ENG, Feb. 10, 2021.

U.S. Appl. No. 63/239,998, filed Sep. 2, 2021.

Infusion Adapter C100, BD Phaseal (Sterile) Medisca downloaded Jul. 30, 2021.

Equashield® II Closed System—Technical Specification Jul. 30, 2021.

Corrected International Search Report and Written Opinion of the International Searching Authority dated Nov. 5, 2024 in Application No. PCT/IL2022/050914.

Extended European Search Report dated Jun. 25, 2025 in application No. 22863788.0.

* cited by examiner 32
94
38
46
48
50
90
70
34
36
60
98
58
72
64
44
54
50
62
84
90
52
42
96
48
56
91
20
55
82
96
66
87
80
53
68
40
85
96
30
86
100

32
96
38
46
90
48
50
36
70
34
60
98
72
58
64
44
54
90
62
50
84
42
52
96
48
87
56
20
91
85
55
66
82
80
53
68
40
86
30
100

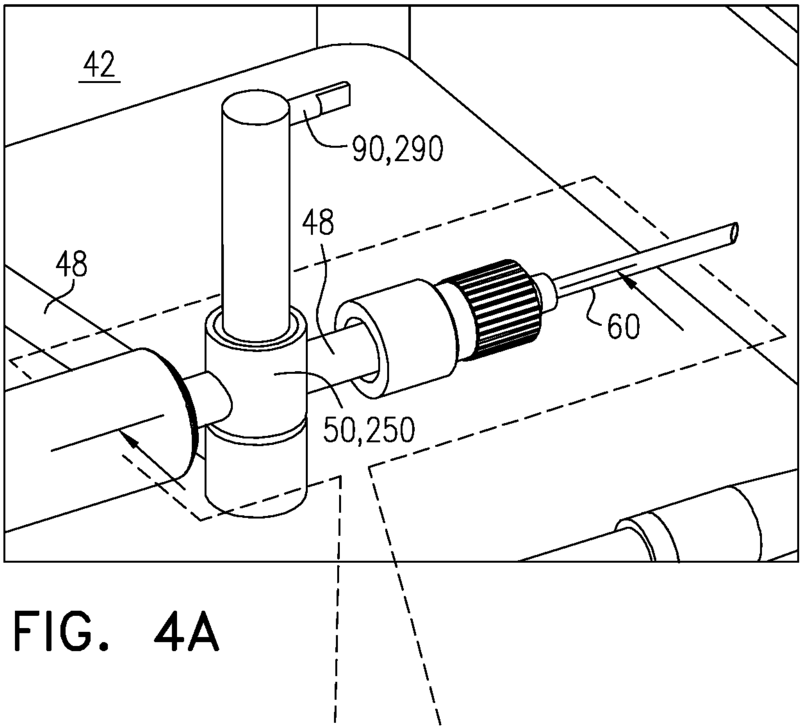
FIG. 4A
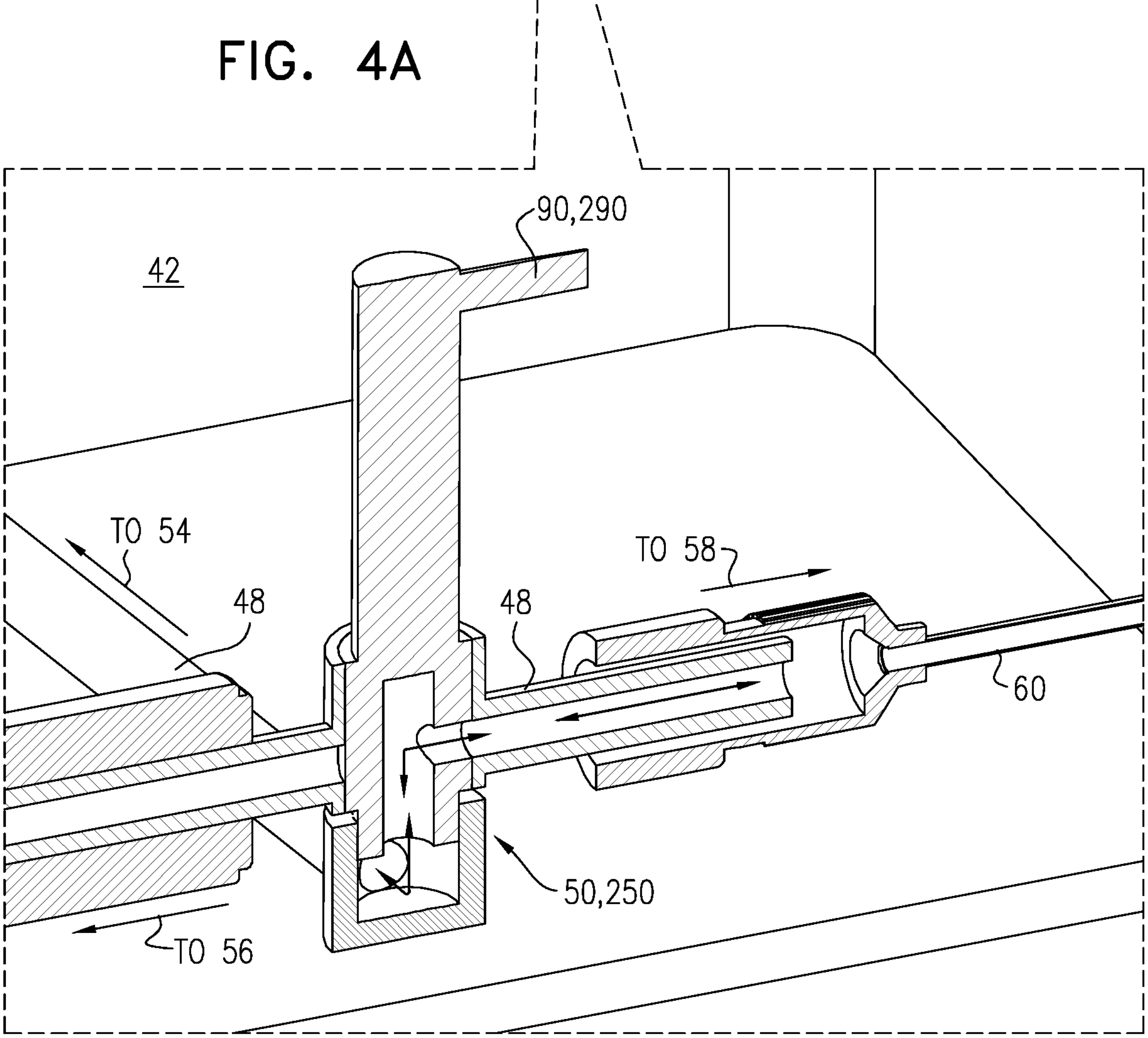

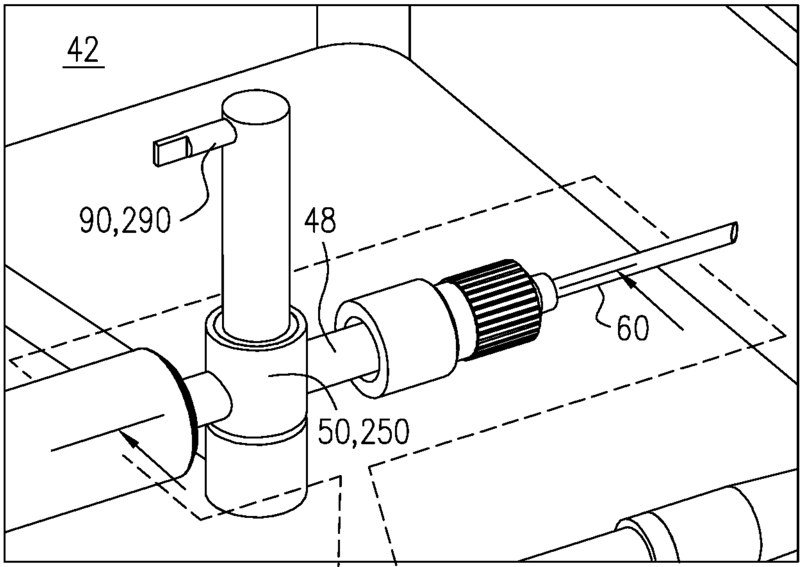
FIG. 4B
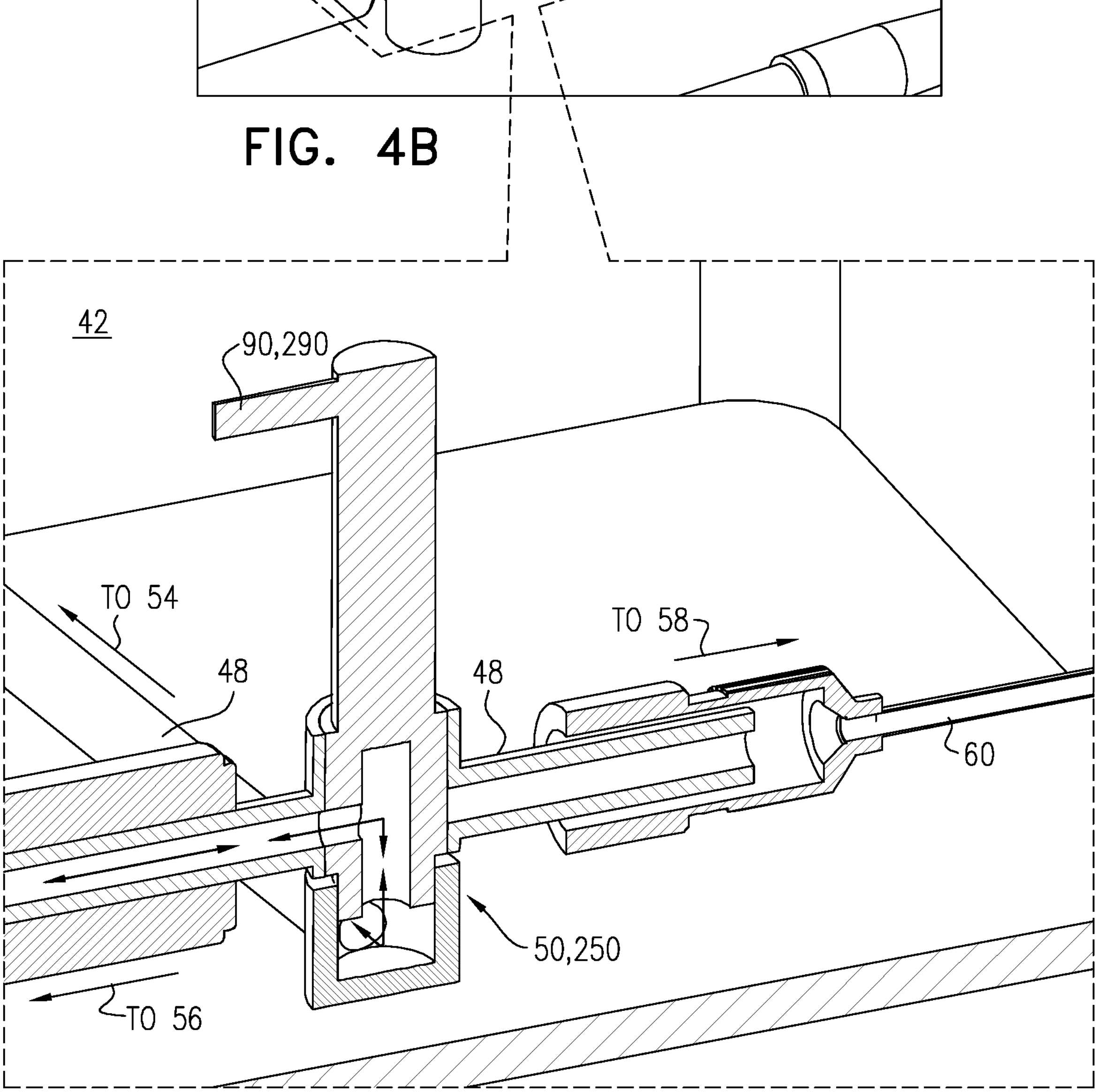

VB
VB
328
322
326
300
318
310

324
328
322
300
318
326
320
310
312
302
314

316

VIB
VIB
326
328
322
300
318
310

300
328
324
322
326
332
320
330
318
312
302
314
310

316

32
94
38
46
70
34
36
60
98
58
72
64
44
54
62
50
84
42
90
52
48
56
20
91
82
66
80
86
53
68
40
300
326
322
100

CLOSED SYSTEM FOR STERILE DRUG PREPARATION AND ADMINISTRATION

CROSS-REFERENCE TO RELATED APPLICATIONS

The present application is the US national stage of International Application PCT/IL2022/050914, filed Aug. 22, 2022, which claims priority from U.S. Provisional Application 63/239,998, filed Sep. 2, 2021, which is assigned to the assignee of the present application and incorporated herein by reference.

FIELD OF THE APPLICATION

The present invention relates generally to techniques for preparation and administration of infusion dosage forms.

BACKGROUND OF THE APPLICATION

Clean rooms are used for the sterile preparation of toxic compounded and other medications, such as IV medications. Clean rooms must provide sterile conditions that ensure the purity and sterility of the medications and protect healthcare workers involved in the preparation of the medications. Clean rooms require specialized air filtration, equipment, and garmented workers.

Australian Patent Application Publication AU 2013200393 A1 to Kriheli describes a method that allows contamination-free transfer of a liquid from one container to another and devices including embodiments of a transfer apparatus and adaptors that are used to carry out the method. By contamination-free transfer of liquid it is meant that during the transfer process there is no leakage of the liquid or air contaminated by the liquid or vapors of the liquid to the surroundings and also that no contaminants from the surroundings come into contact with the liquid. The main advantages of the method, in addition to its simplicity, is that at no stage of the transfer procedure is there leakage of the liquid or air contaminated by the liquid or vapors of the liquid to the surroundings and also that no contaminants from the surroundings come into contact with the liquid. The patent application is described as being particularly directed towards providing an apparatus that is adapted to effect contamination-free transfer of a hazardous drug to and from any container equipped with a standard connector port.

SUMMARY OF THE APPLICATION

Some embodiments of the present invention provide a sterile closed system for drug preparation and administration. The sterile closed system is configured to be coupled to a medication vial and to an infusion bag, and to allow preparation of medication within the system, and delivery of the prepared medication from the system, all without exposure to the outside environment. This system is thus particularly suitable for preparation and administration of dangerous materials, such cytotoxic or antibiotic materials, which can be harmful to the healthcare worker during preparation and administration, and any other drug the preparation and administration of which require sterile conditions.

The sterile closed system comprises an airtight enclosure, which is shaped so as to define an enclosure interior; and an infusion-bag receptacle. An infusion-bag seal is configured, when in a sealing state, to make an airtight seal with respective external surfaces of a medication port and an IV tubing port of a bottom region of the infusion bag, when the medication port and an IV tubing port are inserted into the infusion bag receptacle.

The sterile closed system further comprises;

medication-preparation tubing;

a medication-vial port, which is accessible from outside the airtight enclosure, and which is configured to be sealingly coupled to the medication vial so as to couple the medication vial to the sterile closed system;

a medication-delivery port, which is accessible from outside the airtight enclosure, and which is configured to be sealingly coupled to IV tubing so as to couple the IV tubing to the sterile closed system;

a medication-port-interface needle, disposed within the enclosure interior; and an IV-tubing-port-interface spike, disposed within the enclosure interior.

The medication-preparation tubing is shaped so as to define (a) a syringe-interface end, (b) a medication-vial-interface end, which is in fluid communication with the medication-vial port, and (c) a medication-port-interface end, which is disposed within the enclosure interior, and which is in fluid communication with the medication-port-interface needle.

The sterile closed system further comprises one or more medication-preparation-tubing valves, which regulate flow between the syringe interface end, the medication-vial. interface end, and the medication-port-interface end of the medication-preparation tubing. The sterile closed system further comprises medication-delivery tubing, which is shaped so as to define (a) an IV-tubing-port-interface end, which is disposed within the enclosure interior, and which is in fluid communication with the IV-tubing-port-interface spike, and (b) a medication-delivery end, which is in fluid communication with the medication-delivery port.

The sterile closed system is configured such that, when the infusion-bag seal is in the sealing state:

the medication-port-interface needle is sealingly couplable to the medication port of the infusion bag without breaking the airtight seal between the infusion-bag seal and respective external surfaces of a medication port and an IV tubing port of the infusion bag, and the IV-tubing-port-interface spike is sealingly couplable to the IV tubing port of the infusion bag without breaking the airtight seal between the infusion-bag seal and the respective external surfaces of a medication port and an IV tubing port of the infusion bag.

The sterile closed system thus provides a compact, easy-to-use, disposable replacement for large clean rooms with pressure regimes, airlocks, hoods, and other ancillary equipment. In addition, the healthcare worker needs no personal protective clothing, or only minimal protective clothing. The sterile close system thus may be considered a miniature and disposable clean room, with the addition of drug administration functionality. The sterile closed system may be used to perform the drug preparation at bedside in a patient's room, in a clinic, or in a home, rather than elsewhere, such as in a clean room. Typically, the sterile closed system is single-use. The sterile closed system is typically free of exposed needles, which prevents the risk of injury as a result of sharp needle punctures.

Typically, all of the internal and external components of the sterile closed system are permanently connected to the system and are not disassemble from the system by a healthcare worker before, during or after use of the system. The system is typically provided entirely assembled, without any need for the healthcare worker to couple components of the system together, such as by screwing or otherwise.

The operation of the sterile closed system is convenient. The user of the system, such as a nurse, doctor, pharmacist or technician, does not experience difficulty operating the system, because the operation is clear, safe, accurate and technically convenient at all stages of operation, and thus saves valuable time for medical staff.

For some applications, the activation stages are arranged in sequence so that it is not possible to activate a later stage before an earlier stage. For example, if the drug is provided in dry powder form, the first step of operation is placing the infusion bag and locking it in the infusion-bag receptacle, locking and only then connecting the drug vial to the system, withdrawing a measured volume of fluid and transferring the fluid to the drug vial and so on. until the final stage is administering the drug into the patient's vein.

In an alternative configuration of the present invention, a system is provided that is for use with drugs that are provided in a liquid state, such that there is no need for initial dilution. In this configuration, the system is configured to draw a measured volume equal to the required dose from the drug vial, and transfer it to the infusion bag directly.

In another alterative configuration of the present invention, the system is also be suitable for dilution and drug aspiration directly into the syringe without the need for dilution in an infusion bag.

There is therefore provided, in accordance with an application of the present invention, a sterile closed system for sterile connection to a medication vial and to an infusion bag having an IV tubing port and a medication port extending from a bottom region of the infusion bag, the sterile closed system including:

an airtight enclosure, shaped so as to define an enclosure interior;

an infusion-bag receptacle;

an infusion-bag seal, which is configured, when in a sealing state, to make an airtight seal with respective external surfaces of the medication port and the IV tubing port of the infusion bag, when the medication port and the IV tubing port are inserted at least partially into the infusion-bag receptacle;

a medication-vial port, which is accessible from outside the airtight enclosure, and which is configured to be sealingly coupled to the medication vial so as to couple the medication vial to the sterile closed system;

a medication-port-interface needle, disposed within the enclosure interior;

an IV-tubing-port-interface spike, disposed within the enclosure interior;

medication-preparation tubing, which is shaped so as to define (a) a syringe-interface end, (b) a medication-vial-interface end, which is in fluid communication with medication-vial port, and (c) a medication-port-interface end, which is disposed within the enclosure interior, and which is in fluid communication with the medication-port-interface needle;

one or more medication-preparation-tubing valves, which regulate flow between the syringe-interface end, the medication-vial-interface end, and the medication-port-interface end of the medication-preparation tubing; and medication-delivery tubing, which is shaped so as to define an IV-tubing-port, interface end, which is in fluid communication with the IV-tubing-port-interface spike, wherein the sterile closed system is configured such that, when the infusion-bag seal is in the sealing state:

the medication-port-interface needle is sealingly couplable to the medication port of the infusion bag without breaking the airtight seal between the infusion-bag seal and the respective external surfaces of the medication port and the IV tubing port of the infusion bag, and the IV-tubing-port-interface spike is sealingly couplable to the IV tubing port of the infusion bag without breaking the airtight seal between the infusion-bag seal and the respective external surfaces of the medication port and the IV tubing port of the infusion bag.

For some applications, the medication vial is a glass ampoule, and the medication-vial interface end is configured to be sealingly coupled to the glass ampoule.

For some applications, the sterile closed system does not include any elements that are attachable or detachable during ordinary use.

For some applications, the enclosure interior is configured to withstand positive air pressure with respect to the external atmosphere.

For some applications, the airtight enclosure is configured to allow the medication-port-interface needle and the IV-tubing-port-interface spike to move with respect to the medication port of the infusion bag and the IV tubing port of the infusion bag, respectively, when the infusion-bag seal is in the sealing state.

For some applications, a portion of the airtight enclosure includes a material that is sufficiently flexible to allow the medication-port-interface needle and the IV-tubing-port-interface spike to move with respect to the medication port of the infusion bag and the IV tubing port of the infusion bag, respectively, when the infusion-bag seal is in the sealing state.

For some applications, the infusion-bag seal includes a cover that is rotatable with respect to the infusion-bag receptacle.

For some applications, the sterile closed system includes exactly one medication-preparation-tubing valve, which regulates flow between the syringe-interface end, the medication-vial-interface end, and the medication-port-interface end of the medication-preparation tubing.

For some applications, the airtight enclosure and the infusion-bag receptacle together have a length of no more than 15 cm and a width of no more than 8 cm.

For some applications, the one or more medication-preparation-tubing valves are configured to assume at least:

a first state, in which the one or more medication-preparation-tubing valves (a) allow flow between the syringe-interface end and the medication-port-interface end of the medication-preparation tubing, and (b) block flow (i) between the medication-vial-interface end and the medication-port-interface end and (ii) between the medication-vial-interface end and the syringe-interface end, and a second state, in which the one or more medication-preparation-tubing valves (a) allow flow between the syringe-interface end and the medication-vial-interface end, and (b) block flow (i) between the medication-vial-interface end and the medication-port-interface end and (ii) between the syringe-interface end and the medication-port-interface end.

For some applications, the apparatus further includes a medication-delivery port, which is accessible from outside the airtight enclosure, and the medication-delivery tubing is shaped so as to further define a medication-delivery end, which is in fluid communication with the medication-delivery port.

For some applications, for use with IV tubing, the medication-delivery port is configured to be sealingly coupled to the IV tubing so as to couple the IV tubing to the sterile closed system.

For some applications:

the infusion-bag receptacle is shaped so as to define an infusion-bag receptacle interior, the enclosure interior and the infusion-bag receptacle interior are shaped so as to define a common wall that separates the enclosure interior and the infusion-bag receptacle interior from each other, and the sterile closed system is configured such that, when the infusion-bag seal is in the sealing state:

the medication-port-interface needle is sealingly couplable to the medication port of the infusion bag by penetrating the common wall without breaking the airtight seal between the infusion-bag seal and the respective external surfaces of the medication port and the IV tubing port of the infusion bag, and the IV-tubing-port-interface spike is sealingly couplable to the IV tubing port of the infusion bag by penetrating the common wall without breaking the airtight seal between the infusion-bag seal and the respective external surfaces of the medication port and the IV tubing port of the infusion bag.

For some applications:

the common wall includes a septum, and the sterile closed system is configured such that, when the infusion-bag seal is in the sealing state, the medication-port-interface needle is sealingly couplable to the medication port of the infusion bag by penetrating the septum of the common wall without breaking the airtight seal between the infusion-bag seal and the respective external surfaces of the medication port and the IV tubing port of the infusion bag.

For some applications:

the common wall includes a septum, and the sterile closed system is configured such that, when the infusion-bag seal is in the sealing state, the IV-tubing-port-interface spike is sealingly couplable to the IV tubing port of the infusion bag by penetrating the septum of the common wall without breaking the airtight seal between the infusion bag seal and the respective external surfaces of the medication port and the IV tubing port of the infusion bag.

For some applications, the sterile closed system further includes a syringe, which includes (a) a syringe barrel, which is shaped so as to define a hollow tip permanently sealingly connected in fluid communication with the syringe-interface end of the medication-preparation tubing, and (b) a syringe handle accessible from outside the airtight enclosure.

For some applications, the syringe barrel is located at least partially within the enclosure interior.

For some applications, the sterile closed system is for use with a syringe having a syringe screw-on fitting, and the syringe-interface end of the medication-preparation tubing includes a syringe-interface fitting, which is configured to be sealingly coupled to the syringe screw-on fitting so as to couple the syringe in fluid communication with the syringe-interface end.

For some applications, for use with a syringe having a syringe needle, the syringe-interface end of the medication-preparation tubing includes a septum, which is puncturable by the syringe needle in order to sealingly couple the syringe in fluid communication with the syringe-interface end.

For some applications, the sterile closed system further includes one or more medication-preparation-tubing taps, which are configured to set two or more states of the one or more medication-preparation-tubing valves, and which are manipulable from outside the airtight enclosure.

For some applications, the sterile closed system includes exactly one medication-preparation-tubing tap, which is configured to set the two or more states of the one or more medication-preparation tubing valves.

There is further provided, in accordance with an application of the present invention, a method including:

at least partially inserting a medication port and an IV tubing port that extend from a bottom region of an infusion bag into an infusion-bag receptacle of a sterile closed system, such that (a) an infusion-bag seal of the sterile closed system, when in a sealing state, makes an airtight seal with respective external surfaces of the medication port and the IV tubing port of the infusion bag within the infusion-bag receptacle, wherein the sterile closed system further includes:

an airtight enclosure, shaped so as to define an enclosure interior;

a medication-vial port, which is accessible from outside the airtight enclosure;

a medication-port-interface needle, disposed within the enclosure interior;

an IV-tubing-port-interface spike, disposed within the enclosure interior;

medication-preparation tubing, which is shaped so as to define (a) a syringe-interface end, (b) a medication-vial-interface end, which in fluid communication with medication-vial port, and (c) a medication-port-interface end, which (i) is disposed within the enclosure interior, and (ii) which is in fluid communication with the medication-port-interface needle; and medication-delivery tubing, which is shaped so as to define an IV-tubing-port-interface end, which is in fluid communication with the IV-tubing-port-interface spike;

sealingly coupling the medication-vial port to a medication vial containing a medication, so as to couple the medication vial to the sterile closed system;

while the infusion-bag seal is in the sealing state, sealingly coupling the medication-port-interface needle to the medication port of the infusion bag without breaking the airtight seal between the infusion-bag seal and the respective external surfaces of the medication port and the IV tubing port of the infusion bag;

drawing a volume of IV solution from the infusion bag into a syringe barrel of a syringe sealingly coupled in fluid communication with the syringe-interface end of the medication-preparation tubing, by withdrawing a syringe handle accessible from outside the airtight enclosure;

while the syringe remains sealingly coupled in fluid communication with the syringe-interface end, transferring the volume of the IV solution from the syringe barrel to the medication vial by pushing the syringe handle;

while the medication vial remains coupled to the sterile closed system, agitating the medication vial to mix the medication with the volume of the IV solution to produce a diluted medication;

while the medication vial remains coupled to the sterile closed system and the syringe remains sealingly coupled in fluid communication with the syringe-interface end, transferring the diluted medication from the medication vial to the syringe barrel by withdrawing the syringe handle;

while the syringe remains sealingly coupled in fluid communication with the syringe-interface end, transferring the diluted medication from the syringe barrel to the infusion bag by pushing the syringe handle; and while the infusion-bag seal is in the sealing state, sealingly coupling the IV-tubing-port-interface spike to the IV tubing port of the infusion bag without breaking the airtight seal between the infusion-bag seal and the respective external surfaces of the medication port and the IV tubing port of the infusion bag.

For some applications, sealingly coupling the IV-tubing-port-interface spike to the IV tubing port includes breaking off a break-off port cap of the IV tubing port while the infusion-bag seal is in the sealing state and the break-off port cap is within the infusion-bag receptacle.

For some applications, the method further includes creating, within the enclosure interior, positive air pressure with respect to the external atmosphere.

For some applications, the medication vial is a glass ampoule, and sealingly coupling the medication-vial-interface end to the medication vial includes sealingly coupling the medication-vial-interface end in glass ampoule.

For some applications, the method does not include attaching to or detaching from the sterile closed system any elements other than the infusion bag and the medication vial.

For some applications, the airtight enclosure is configured to allow the medication-port-interface needle and the IV-tubing-port-interface spike to move with respect to the medication port of the infusion bag and the IV tubing port of the infusion bag, respectively, when the infusion-bag seal is in the sealing state.

For some applications, a portion of the airtight enclosure includes a material that is sufficiently flexible to allow the medication-port-interface needle and the IV-tubing-port-interface spike to move with respect to the medication port of the infusion bag and the IV tubing port of the infusion bag, respectively, when the infusion-bag seal is in the sealing state.

For some applications, the sterile closed system further includes a medication-delivery port, which is accessible from outside the airtight enclosure, and the medication-delivery tubing is shaped so as to further define a medication-delivery end, which is in fluid communication with the medication-delivery port.

For some applications, the method further includes sealingly coupling IV tubing to the medication-delivery port.

For some applications, sealingly coupling the IV tubing to the medication-delivery port includes sealingly coupling the IV tubing to the medication-delivery port while the medication vial remains coupled to the sterile closed system.

For some applications, the method further includes performing an infusion via the IV tubing.

For some applications, performing the infusion via the IV tubing includes performing an entirety of the infusion via the IV tubing while the medication vial remains coupled to the sterile closed system.

For some applications, the method does not include attaching to or detaching from the sterile closed system any elements other than the infusion bag, the medication vial, and the IV tubing.

For some applications:

the sterile closed system further includes one or more medication-preparation-tubing valves, which regulate flow between the syringe-interface end, the medication-vial-interface end, and the medication-port-interface end of the medication-preparation tubing, drawing the volume of the IV solution from the infusion bag into the syringe barrel includes drawing the volume of the IV solution from the infusion bag into the syringe barrel while the one or more medication-preparation-tubing valves are in a first state, in which the one or more medication-preparation-tubing valves (a) allow flow between the syringe-interface end and the medication-port-interface end of the medication-preparation tubing, and (b) block flow (i) between the medication-vial-interface end and the medication-port-interface end and (ii) between the medication-vial-interface end and the syringe-interface end, transferring the volume of the IV solution from the syringe barrel to the medication vial includes transferring the volume of the IV solution from the syringe barrel to the medication vial while the one or more medication-preparation-tubing valves are in a second state, in which the one or more medication-preparation-tubing valves (a) allow flow between the syringe-interface end and the medication-vial-interface end, and (b) block flow (i) between the medication-vial-interface end and the medication-port-interface end and (ii) between the syringe-interface end and the medication-port interface end, transferring the diluted medication from the medication vial to the syringe barrel includes transferring the diluted medication from the medication vial to the syringe barrel while the one or more medication-preparation-tubing valves are in the second state, and transferring the diluted medication from the syringe barrel to the infusion bag includes transferring the diluted medication from the syringe barrel to the infusion bag while the one or more medication-preparation-tubing valves are in the first state.

For some applications, the method further includes setting the first and the second states using one or more medication-preparation-tubing taps that are manipulable from outside the airtight enclosure.

For some applications, setting the first and the second states using the one or more medication-preparation-tubing taps includes setting the first and the second states using exactly one medication-preparation-tubing tap that is manipulable from outside the airtight enclosure.

For some applications, inserting the medication port and the IV tubing port of the infusion bag into the infusion-bag receptacle such that the infusion-bag seal of the sterile closed system makes the airtight seal with the respective external surfaces of the medication port and the IV tubing port of the infusion bag includes:

inserting the medication port and the IV tubing port of the infusion bag into the infusion-bag receptacle while the infusion-bag seal is in a non-sealing state; and thereafter, transitioning the infusion-bag seal to the sealing state.

For some applications, transitioning the infusion-bag seal to the sealing state includes rotating a cover of the infusion-bag seal with respect to the infusion-bag receptacle.

For some applications, the method further includes sealingly coupling IV tubing to the medication-delivery port so as to couple the IV tubing to the sterile closed system.

For some applications:

the infusion-bag receptacle is shaped so as to define an infusion-bag receptacle interior, the enclosure interior and the infusion-bag receptacle interior are shaped so as to define a common wall that separates the enclosure interior and the infusion-bag receptacle interior from each other, sealingly coupling the medication-port-interface needle to the medication port of the infusion bag includes penetrating the common wall without breaking the airtight seal between the infusion-bag seal and the respective external surfaces of the medication port and the IV tubing port of the infusion bag, and sealingly coupling the IV-tubing-port-interface spike to the IV tubing port of the infusion bag includes penetrating the common wall without breaking the airtight seal between the infusion-bag seal and the respective external surfaces of the medication port and the IV tubing port of the infusion bag.

For some applications:

the common wall includes a septum, and sealingly coupling the medication-port-interface needle to the medication port of the infusion bag includes penetrating the septum of the common wall without breaking the airtight seal between the infusion-bag seal and the respective external surfaces of the medication port and the IV tubing port of the infusion bag.

For some applications, the common wall includes a septum, and sealingly coupling the IV-tubing-port-interface spike to the IV tubing port of the infusion bag includes penetrating the septum of the common wall without breaking the airtight seal between the infusion-bag seal and the respective external surfaces of the medication port and the IV tubing port of the infusion bag.

For some applications, the method further includes, before drawing the volume of IV solution from the infusion bag into the syringe barrel, sealingly coupling a syringe screw-on fitting of the syringe to a syringe-interface fitting of the syringe-interface end of the medication-preparation tubing.

For some applications, the method further includes, before drawing the volume of IV solution from the infusion bag into the syringe barrel, sealingly coupling a syringe needle of the syringe to a septum of the syringe-interface end of the medication-preparation tubing by puncturing the syringe needle through the septum.

There is further provided, in accordance with an application of the present invention, a glass ampoule adapter for use with a glass ampoule, the glass ampoule adapter including:

a flexible proximal elongate body enclosure, which has an elongate interior shaped so as to accept and enclose a body of the glass ampoule, and which is shaped so as to define an insertion opening through which the glass ampoule body is insertable into the elongate interior;

a flexible neck enclosure, which is shaped so as to make an airtight seal with a neck of the glass ampoule when the glass ampoule body is inserted into the elongate interior;

a flexible distal elongate tip enclosure, which is sealingly coupled to the proximal elongate body enclosure by the flexible neck enclosure, and which is shaped so as to accept and enclose a tip of the glass ampoule when the glass ampoule body is inserted into the elongate interior; and a flexible septum, which extends radially outward from an external lateral surface of the distal elongate tip enclosure, wherein the glass ampoule adapter is configured such that, when the glass ampoule is within the glass ampoule adapter, sideways movement of the distal elongate tip enclosure:

deflects the glass ampoule tip sideways with respect to the glass ampoule body, thereby breaking the glass ampoule neck and snapping the glass ampoule tip off the glass ampoule body to create a distal opening in the glass ampoule body, and aligns the flexible septum with the glass ampoule body and forms a seal with the broken glass ampoule neck, thereby sealing the distal opening of the glass ampoule body.

For some applications, the flexible proximal elongate body enclosure, the flexible neck enclosure, and the flexible distal elongate tip enclosure are integrally formed from a single piece of flexible material.

For some applications, the flexible septum, the flexible proximal elongate body enclosure, the flexible neck enclosure, and the flexible distal elongate tip enclosure are integrally formed from the single piece of flexible material.

There is further provided, in accordance with an application of the present invention, a method including:

inserting a body of a glass ampoule into a flexible proximal elongate body enclosure of a glass ampoule adapter, via an insertion opening of the flexible proximal elongate body enclosure, such that:

an elongate interior of the flexible proximal elongate body enclosure encloses the glass ampoule body, a flexible neck enclosure of the glass ampoule adapter makes an airtight seal with a neck of the glass ampoule, a flexible distal elongate tip enclosure of the glass ampoule adapter accepts and encloses a tip of the glass ampoule, wherein the flexible distal elongate tip enclosure is sealingly coupled to the proximal elongate body enclosure by the flexible neck enclosure, and a flexible septum of the glass ampoule adapter extends radially outward from an external lateral surface of the distal elongate tip enclosure; and when the glass ampoule is within the glass ampoule adapter, moving the distal elongate tip enclosure sideways, so as to:

deflect the glass ampoule tip sideways with respect to the glass ampoule body, thereby breaking the glass ampoule neck and snapping the glass ampoule tip off the glass ampoule body to create a distal opening in the glass ampoule body, and align the flexible septum with the glass ampoule body and forms a seal with the broken glass ampoule neck, thereby sealing the distal opening of the glass ampoule body.

The present invention will be more fully understood from the following detailed description of embodiments thereof, taken together with the drawings, in which:

BRIEF DESCRIPTION OF THE DRAWINGS

FIGS. 4A-B are schematic illustrations of a medication-preparation-tubing valve and a medication-preparation-tubing tap of the sterile closed system of FIG. 1, in accordance with an application of the present invention;

DETAILED DESCRIPTION OF APPLICATIONS

Figure 1:
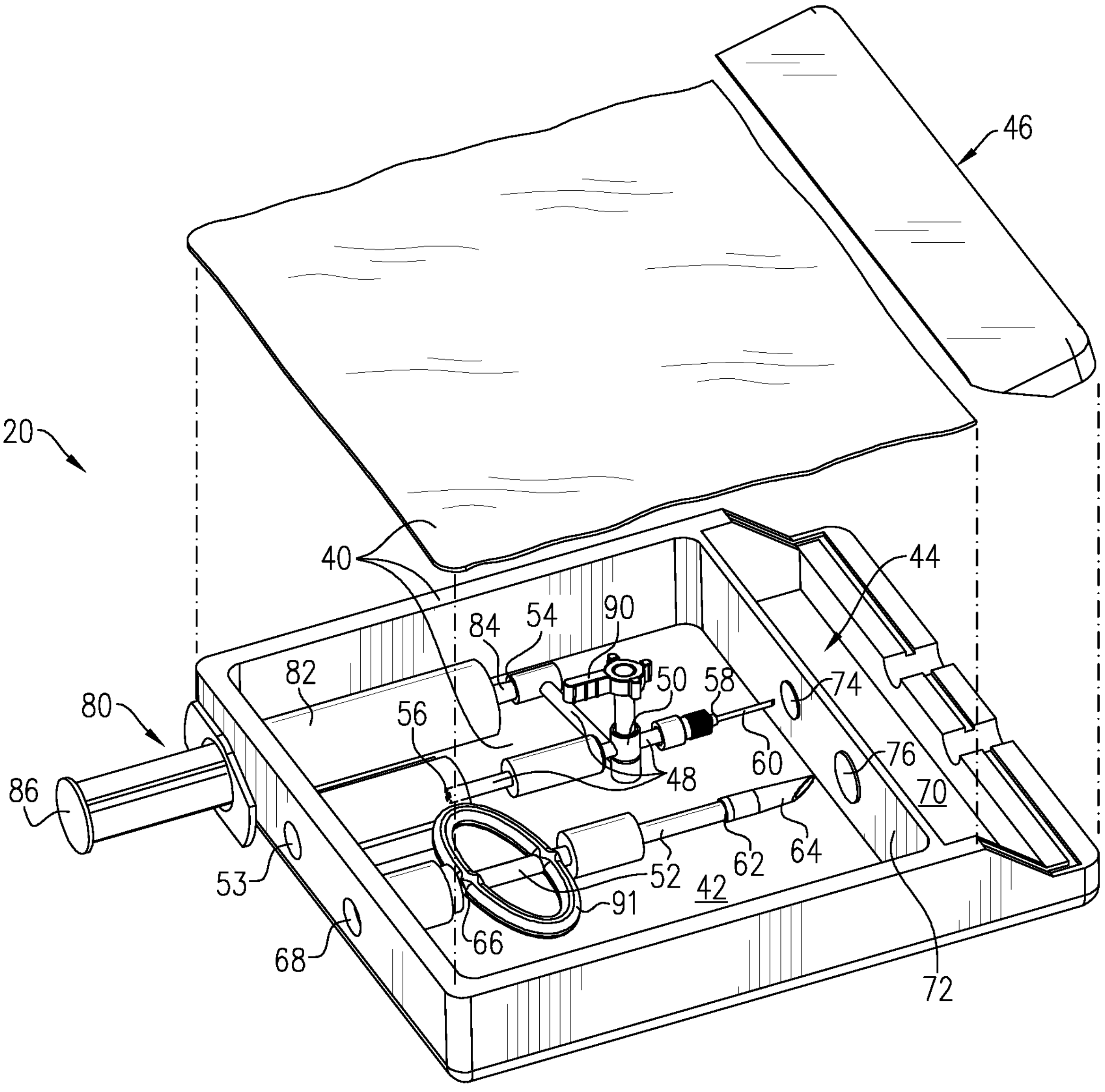
FIG. 1 is a schematic illustration of a sterile closed system for sterile drug preparation and administration, in accordance with an application of the present invention.

FIG. 1 is a schematic illustration of a sterile closed system 20 for sterile drug preparation and administration, in accordance with an application of the present invention. Sterile closed system 20 is configured for sterile connection to a medication vial 30, such as described hereinbelow with reference to FIG. 2D, and to an infusion bag 32 having a medication port 36 and an IV tubing port 34 extending from a bottom region 38 of infusion bag 32, such as described hereinbelow with reference to FIG. 2A.

Sterile closed system 20 comprises:

- an airtight enclosure 40, shaped so as to define an enclosure interior 42;
- an infusion-bag receptacle 44;
- an infusion-bag seal 46;
- medication-preparation tubing 48;
- one or more medication-preparation-tubing valves 50;
- medication-delivery tubing 52;
- a medication-vial port 53, which is accessible from outside airtight enclosure 40, and which is configured to be sealingly coupled to medication vial 30 so as to couple medication vial 30 to sterile closed system 20;
- optionally, a medication-delivery port 68, which is accessible from outside airtight enclosure 40, and which is configured to be sealingly coupled to IV tubing 100 so as to couple IV tubing 100 to sterile closed system 20;
- a medication-port-interface needle 60, disposed within enclosure interior 42; and
- an IV-tubing-port-interface spike 64, disposed within enclosure interior 42.

Infusion-bag seal 46 is configured, when in a sealing state (such as shown in FIGS. 2C-K, described hereinbelow), to make an airtight seal with respective external surfaces of medication port 36 and IV tubing port 34 of infusion bag 32, when medication port 36 and IV tubing port 34 are within infusion-bag receptacle 44 (such as shown in FIGS. 2B-K, described hereinbelow).

Optionally, all or a portion of airtight enclosure 40 is transparent. For example, all or a portion of an upper wall (e.g., a cover) of airtight enclosure 40 may be transparent.

For some applications, infusion-bag seal 46 comprises a cover (e.g., a door) that is rotatable with respect to infusion-bag receptacle 44. The rotatable cover may function as a lever, or it may not function as a lever. Infusion-bag seal 46 may be lockably couplable to infusion-bag receptacle 44 (e.g., by snapping).

For some applications, infusion-bag receptacle 44 is configured for use with a particular type of infusion bag, such as a type that is commercially available from a manufacturer, e.g., Baxter International Inc. or B. Braun Medical Inc. Thus, for some applications, a plurality of different configurations of sterile closed system 20 are provided, each configured to be used with a respective type of infusion bag provided by a respective manufacturer.

For example, for Baxter IV bags, there is a uniform shape for all the different volumes (e.g., 100, 250, 500, and 1000 ml), i.e., bottom region 38 of Baxter bags comprises a hard material part and that is identical in all different volumes in terms of structure and shape.

Typically, airtight enclosure 40 is universal, in the sense that it does not vary based on the particular type of infusion bag with which it is used.

Medication-preparation tubing 48 is shaped so as to define:

- a syringe-interface end 54,
- a medication-vial-interface end 56, which is in fluid communication with medication-vial port 53, and
- a medication-port-interface end 58, which is disposed within enclosure interior 42, and which is in fluid communication with medication-port-interface needle 60.

The one or more medication-preparation-tubing valves 50 regulate flow between syringe-interface end 54, medication-vial-interface end 56, and medication-port-interface end 58 of medication-preparation tubing 48.

Medication-delivery tubing 52 is shaped so as to define:

- an IV-tubing-port-interface end 62, which is disposed within enclosure interior 42, and which is in fluid communication with IV-tubing-port-interface spike 64, and
- optionally, a medication-delivery end 66, which is in fluid communication with medication-delivery port 68 in configurations in which medication-delivery port 68 is provided.

(As is known in the art, spikes differ from needles in that spikes are thicker than needles, typically comprise plastic or another non-metallic material, have wider flow openings than needles.)

Reference is made to FIGS. 2C-K, which are described hereinbelow in more detail. Sterile closed system 20 is configured such that, when infusion-bag seal 46 is in the sealing state:

- medication-port-interface needle 60 is sealingly couplable to medication port 36 of infusion bag 32 without breaking the airtight seal between infusion-bag seal 46 and the respective external surfaces of medication port 36 and IV tubing port 34 of infusion bag 32, and
- IV-tubing-port-interface spike 64 is sealingly couplable to IV tubing port 34 of infusion bag 32 without breaking the airtight seal between the respective external surfaces of medication port 36 and IV tubing port 34 of infusion bag 32.

Reference is again made to FIG. 1, and is also made to FIGS. 2D and 2K, which are described hereinbelow in more detail. Typically, airtight enclosure 40 is configured to allow medication-port-interface needle 60 and IV-tubing-port-interface spike 64 to move with respect to medication port 36 of infusion bag 32 and IV tubing port 34 of infusion bag 32, respectively, when infusion-bag seal 46 is in the sealing state. For example, a portion of airtight enclosure 40 may comprise a material that is sufficiently flexible to allow medication-port-interface needle 60 and IV-tubing-port-interface spike 64 to move with respect to medication port 36 of infusion bag 32 and IV tubing port 34 of infusion bag 32, respectively, when infusion-bag seal 46 is in the sealing state. For example, the material may comprise polypropylene glycol or VIAFLEX plastic (which comprises a specially formulated polyvinyl chloride (p1-146plastic)). Alternatively or additionally, airtight enclosure 40 may be shaped so as to define accordion pleats and/or one or more hinges to allow this movement. Alternatively or additionally, airtight enclosure 40, common wall 72, and/or infusion-bag receptacle 44 may be configured to allow movement of medication port 36 and/or IV tubing port 34 to move with respect to medication-port-interface needle 60 and IV-tubing-port-interface spike 64, respectively.

For some applications, airtight enclosure 40 comprises tracks that direct the motion of medication-port-interface needle 60 and IV-tubing-port-interface spike 64 with respect to medication port 36 of infusion bag 32 and IV tubing port 34 of infusion bag 32, respectively, when infusion-bag seal 46 is in the sealing state.

For some applications, sterile closed system 20 comprises, in addition to medication-port-interface needle 60, an air return needle (configuration not shown). For example, the two needles may be arranged as in the Equashield® Vial Adaptor (Equashield LLC, Port Washington, NY, USA).

For some applications, sterile closed system 20 comprises a female adapter, in which medication-port-interface needle 60 is disposed behind a septum, such as is known in the vial adapter art. For example, the female adapter may be similar to a Teva Syringe Adaptor (Tevadaptor®/Simpliva) (Teva Medical Ltd., Kiryat Shmona, Israel).

Reference is again made to FIG. 1. For some applications, infusion-bag receptacle 44 is shaped so as to define an infusion-bag receptacle interior 70. Enclosure interior 42 and infusion-bag receptacle interior 70 are shaped so as to define a common wall 72 that separates enclosure interior 42 and infusion-bag receptacle interior 70 from each other. Sterile closed system 20 is configured such that, when infusion-bag seal 46 is in the sealing state:

- medication-port-interface needle 60 is sealingly couplable to medication port 36 of infusion bag 32 by penetrating common wall 72 without breaking the airtight seal between infusion-bag seal 46 and the respective external surfaces of medication port 36 and IV tubing port 34 of infusion bag 32, such as described hereinbelow with reference to FIG. 2F, and
- IV-tubing-port-interface spike 64 is sealingly couplable to IV tubing port 34 of infusion bag 32 by penetrating common wall 72 without breaking the airtight seal between infusion-bag seal 46 and the respective external surfaces of medication port 36 and IV tubing port 34 of infusion bag 32, such as described hereinbelow with reference to FIG. 2J.

For some of these applications, common wall 72 comprises a first septum 74. Sterile closed system 20 is configured such that, when infusion-bag seal 46 is in the sealing state, medication-port-interface needle 60 is sealingly couplable to medication port 36 of infusion bag 32 by penetrating first septum 74 of common wall 72 without breaking the airtight seal between infusion-bag seal 46 and the respective external surfaces of medication port 36 and IV tubing port 34 of infusion bag 32.

Alternatively or additionally, for some applications, common wall 72 comprises a second septum 76. Sterile closed system 20 is configured such that, when infusion-bag seal 46 is in the sealing state, IV-tubing-port-interface spike 64 is sealingly couplable to IV tubing port 34 of infusion bag 32 by penetrating second septum 76 of common wall 72 without breaking the airtight seal between infusion-bag seal 46 and the respective external surfaces of medication port 36 and IV tubing port 34 of infusion bag 32.

Reference is still made to FIG. 1. For some applications, sterile closed system 20 further comprises a syringe 80, which comprises:

- a syringe barrel 82, which is shaped so as to define a hollow tip 84 permanently sealingly connected in fluid communication with syringe-interface end 54 of medication-preparation tubing 48 (and, typically, at least one syringe plunger 85, which comprises a plunger head 87 (labeled in FIG. 2H) disposed within syringe barrel 82), and
- a syringe handle 86 accessible from outside airtight enclosure 40.

In this configuration, the permanent attachment of syringe 80 to the other elements of sterile closed system 20 may facilitate efficient use of the system by reducing assembly time, and may also reduce the risk of leakage and contamination by providing a tight connection between the syringe and the other elements.

Reference is still made to FIG. 1. For some applications, syringe barrel 82 is located at least partially within (e.g., mostly within or entirely within) enclosure interior 42. Alternatively, syringe barrel 82 is located at least partially outside enclosure interior 42, such as described hereinbelow with reference to FIG. 3.

For other applications, a separate syringe is coupled to the system during use, such as described hereinbelow with reference to FIG. 3.

Reference is still made to FIG. 1. For some applications, sterile closed system 20 further comprises one or more medication-preparation-tubing taps 90, which are configured to set two or more states of the one or more medication-preparation-tubing valves 50, and which are manipulable from outside airtight enclosure 40. For some applications, the one or more medication-preparation-tubing taps 90 are disposed entirely within enclosure interior 42 of airtight enclosure 40 and are configured to be manipulated from outside airtight enclosure 40 by manipulating a flexible wall of airtight enclosure 40. Alternatively, for other applications, the one or more medication-preparation-tubing taps 90 are disposed outside enclosure interior 42 (via one or more respective airtight seals) and are configured to be manipulated from outside airtight enclosure 40. For some applications, the one or more medication-preparation-tubing taps 90 and syringe handle 86 are the only elements of sterile closed system 20 accessible by the healthcare worker from outside the system. For other applications, syringe handle 86 is the only element of sterile closed system 20 accessible by the healthcare worker from outside the system.

For some applications, sterile closed system 20 does not comprise any elements that are attachable or detachable during ordinary use. In these applications, sterile closed system 20 is provided preassembled as one part, without the need for any assembly.

For some applications, enclosure interior 42 is configured to withstand positive air pressure with respect to the external atmosphere, such as described hereinbelow with reference to FIG. 2C.

For some applications, airtight enclosure 40 and infusion-bag receptacle 44 together have a length of at least 5 cm, no more than 15 cm, and/or 5-15 cm, e.g., 10 cm; a width of at least 3 cm, no more than 8 cm, and/or 3-8 cm, e.g., 5 cm; and/or a depth of at least 2 cm, no more than 5 cm, and/or 2-5 cm, e.g., 3.5 cm. Optionally, airtight enclosure 40 and an infusion-bag receptacle 44 together are rectangular, although other shapes are possible.

For some applications, sterile closed system 20 further comprises one or more loops 91 disposed within enclosure interior 42 along medication delivery tubing 52, which may provide ergonomic gripping for moving IV-tubing-port-interface spike 64 toward IV tubing port 34 of infusion bag 32 and applying force to penetrate the spike into the medication port. The one or more loops 91 do not play a functional role in fluid flow through medication-delivery tubing 52.

Figure 2A:
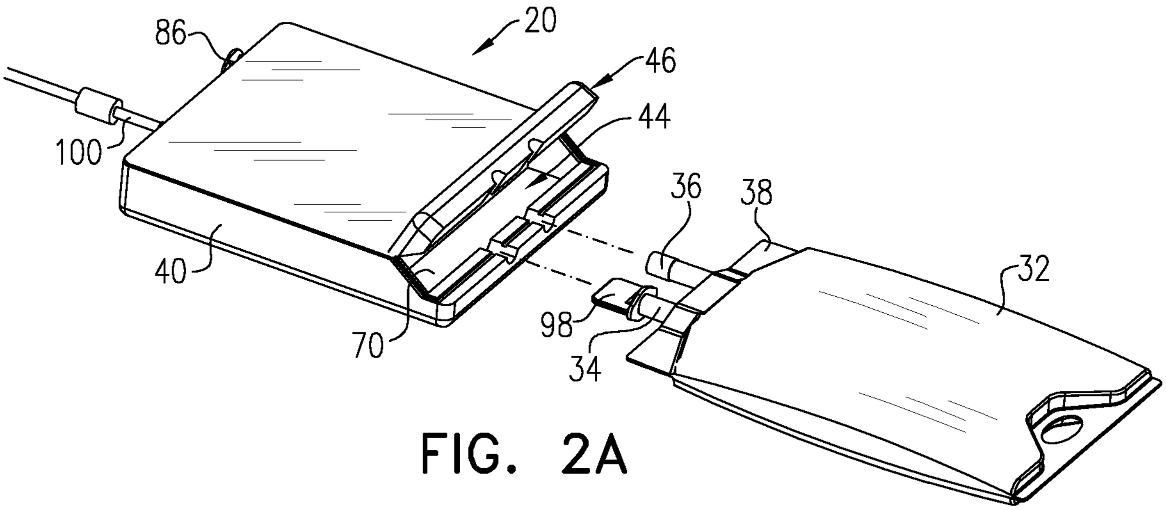
FIGS. 2A-L are schematic illustrations of a method of using the sterile closed system of FIG. 1, in accordance with an application of the present invention.

Reference is now made to FIGS. 2A-L, which are schematic illustrations of a method of using sterile closed system 20, in accordance with an application of the present invention. FIG. 2A shows sterile closed system 20 and infusion bag 32 before they have been coupled together. Infusion bag 32 is typically not an element of sterile closed system 20, and is typically a conventional 2-port infusion bag having medication port 36 and IV tubing port 34 extending from bottom region 38 of the bag. Sterile closed system 20 may be single-use and disposable, such as to prevent contamination that might be caused by re-use.

As shown in FIG. 28, while infusion-bag seal 46 is open, in a non-sealing state, medication port 36 and IV tubing port 34 of infusion bag 32, which extend from bottom region 38, are within infusion-bag receptacle 44. Medication port 36 and IV tubing port 34 of infusion bag 32 should be disinfected, such as with alcohol, before being inserted into infusion-bag receptacle 44.

Figure 2B:
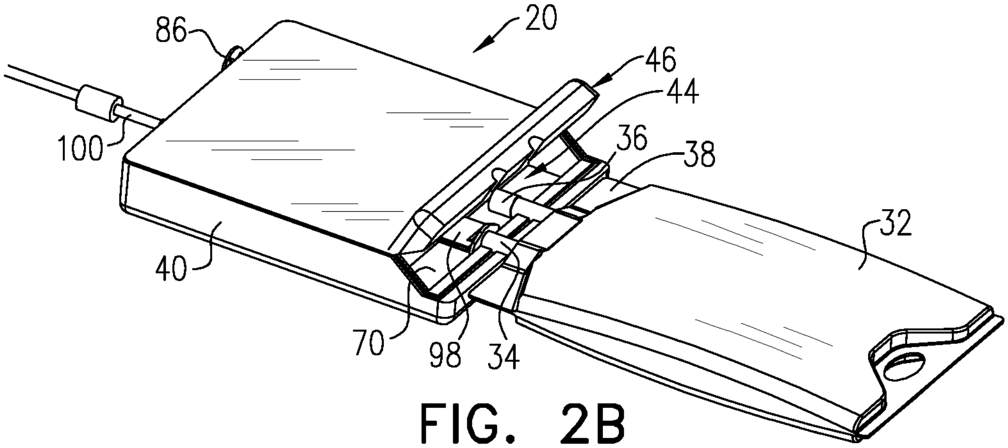
Figure 2C:
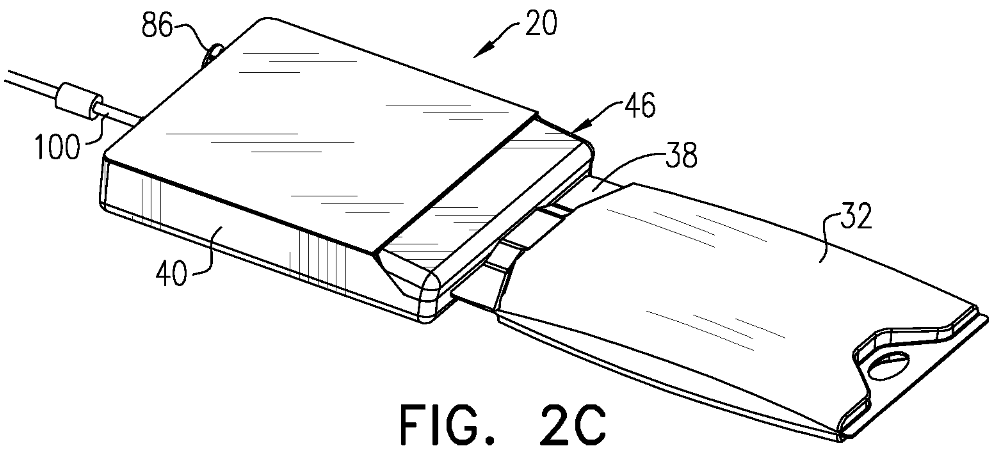

As shown in FIG. 2C, infusion-bag seal 46 is closed so as to transition from the non-sealing state to a sealing state, in which infusion-bag seal 46 makes an airtight seal with the respective external surfaces of medication port 36 and IV tubing port 34 of infusion bag 32, while medication port 36 and IV tubing port 34 of infusion bag 32 are enclosed within infusion-bag receptacle 44.

Optionally, positive air pressure with respect to the external atmosphere is created within enclosure interior 42, such as by filling enclosure interior 42 with a gas, typically an inert gas, e.g., nitrogen. Positive pressure inside enclosure interior 42 may help prevent polluted outside ambient air from entering the enclosure interior, especially when moving the needle and spike towards the infusion bag, at the stage when the septum is penetrated, thereby ensuring a very high level of sterility. However, it is not necessary to create the positive air pressure.

Figure 2D:
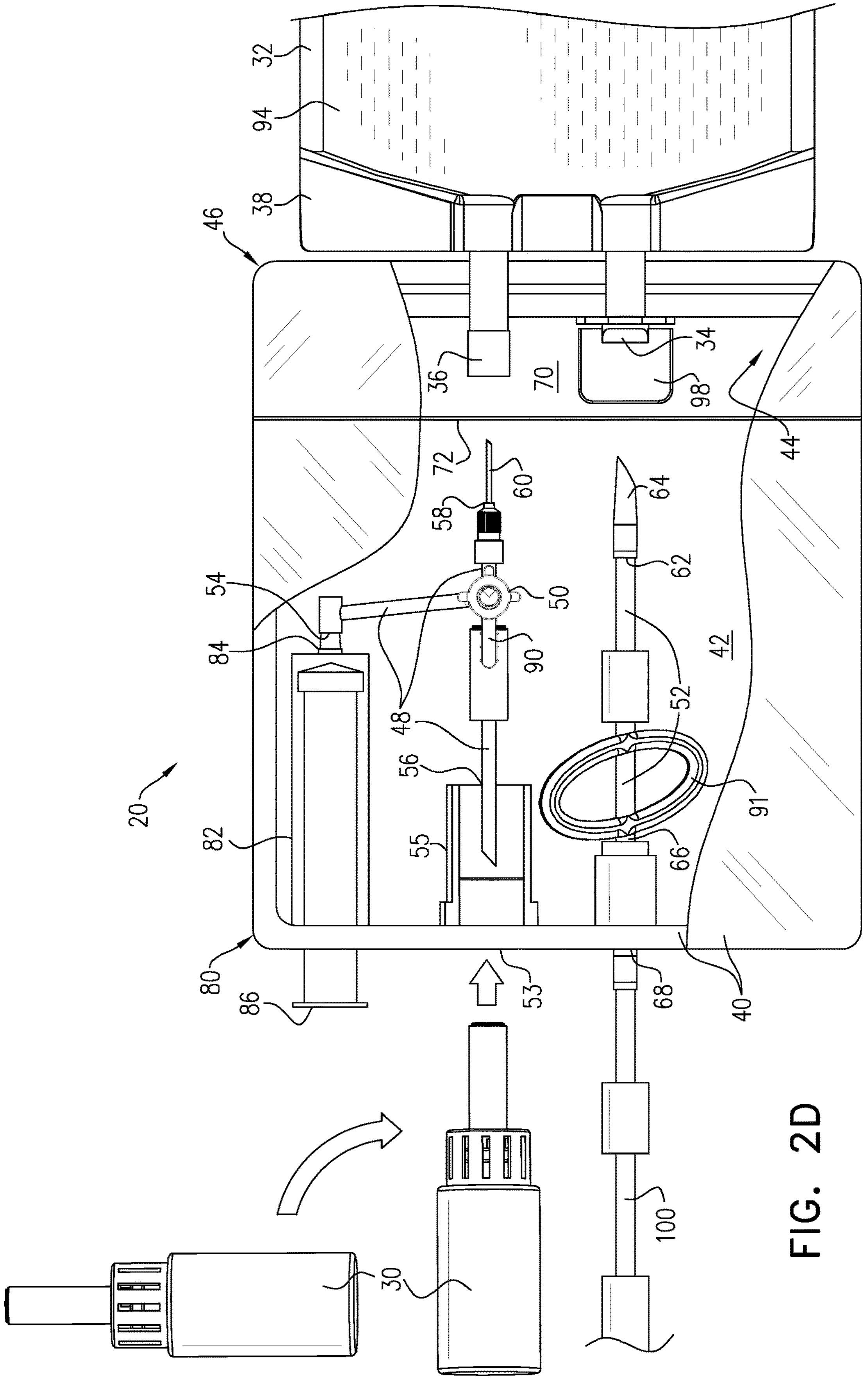
Figure 2E:
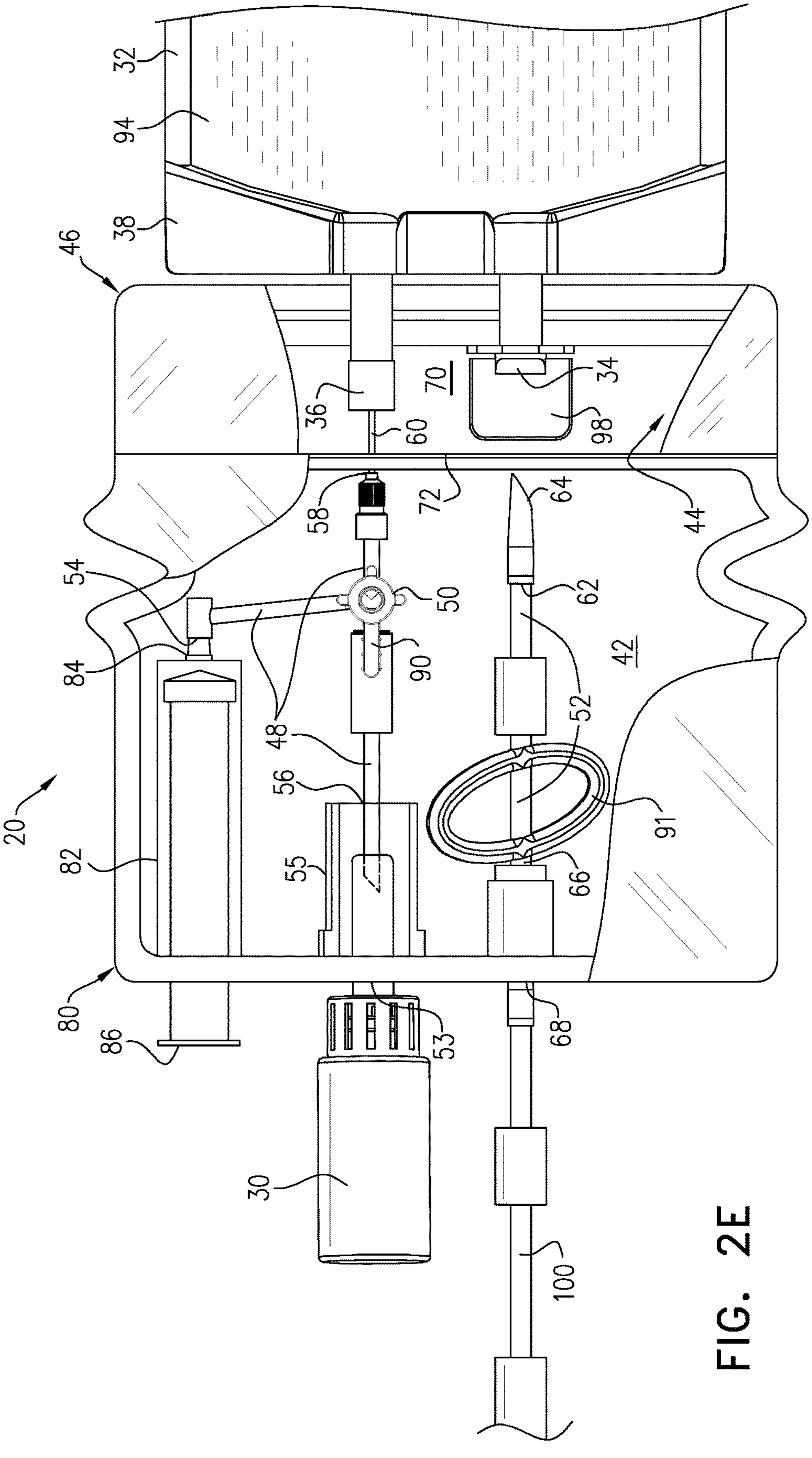

As shown in FIGS. 2D-E, medication vial 30, containing a medication, is sealingly coupled to medication-vial port 53, so as to couple medication vial 30 to sterile closed system 20. Typically, medication-vial port 53 comprises a sterile vial adapter, as is known the art and commercially available. For example, the adapter may be an Equashield® Vial Adaptor (Equashield LLC, Port Washington, NY, USA) or a Teva Vial Adaptor (Tevadaptor®/Simpliva) (Teva Medical Ltd., Kiryat Shmona, Israel). To this end, medication-vial port 53 typically comprises a female vial-adapter receptacle 55, that is configured to receive a male part of the vial adapter. Medication vial 30 is typically not an element of sterile closed system 20, and is typically conventional. The medication may, for example, be a liquid or a powder, as is known in the art.

Figure 2F:
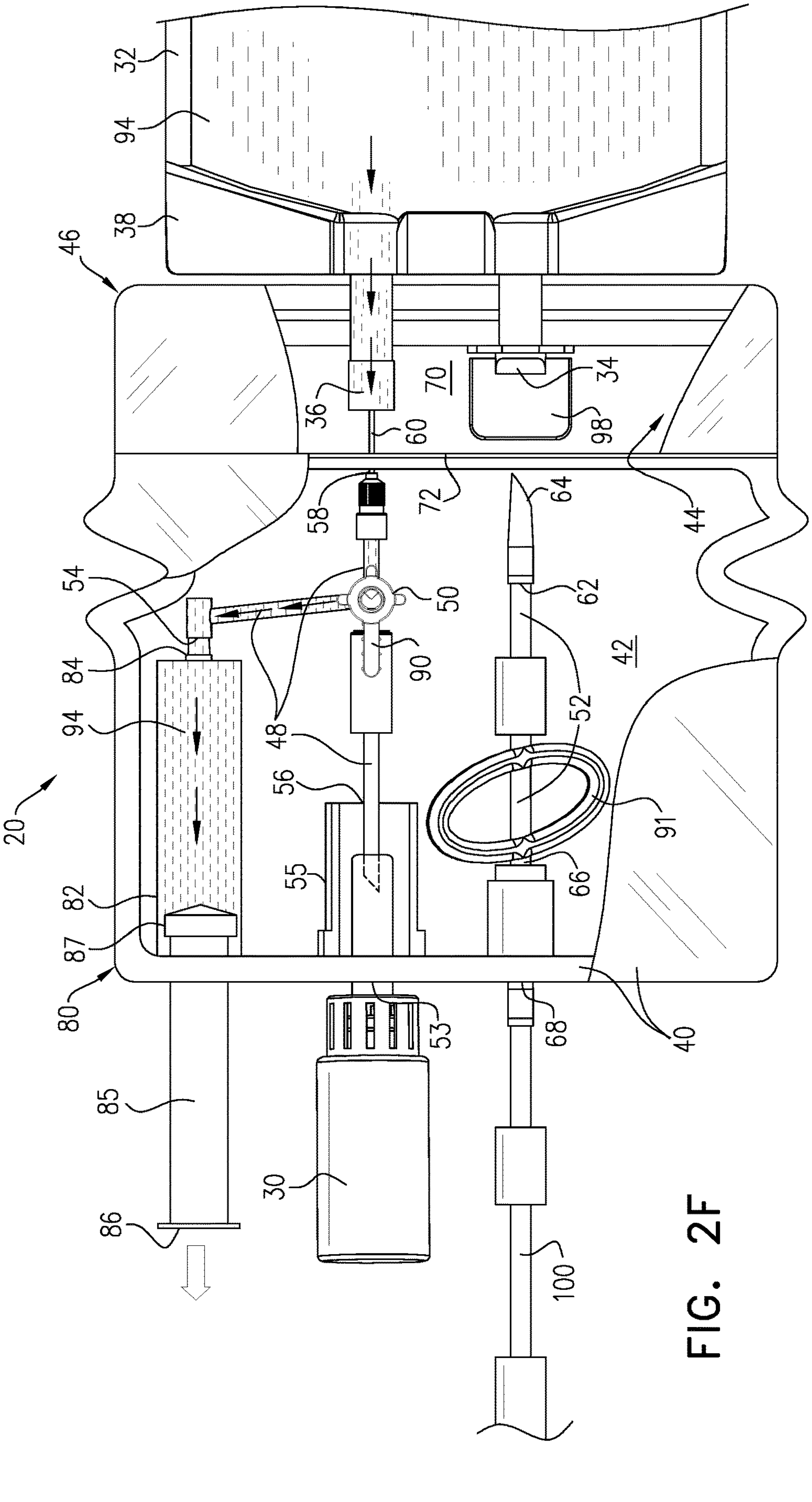

As shown in FIG. 2F, while infusion-bag seal 46 is in the sealing state, medication-port-interface needle 60 is sealingly coupled to medication port 36 of infusion bag 32 without breaking the airtight seal between infusion-bag seal 46 and the respective external surfaces of medication port 36 and IV tubing port 34 of infusion bag 32. As described hereinabove with reference to FIG. 1, airtight enclosure 40 is typically configured to allow medication-port-interface needle 60 to move with respect to medication port 36 of infusion bag 32 when infusion-bag seal 46 is in the sealing state. Typically, mechanical action external to the system is used to sealingly couple medication-port-interface needle 60 to medication port 36 of infusion bag 32. This step of the method may be performed before or after the step of the method described hereinabove with reference to FIGS. 2D-E.

For some applications, sealingly coupling IV-tubing-port-interface spike 64 to IV tubing port 34 comprises breaking off a break-off port cap 98 of IV tubing port 34 while infusion-bag seal 46 is in the sealing state and break-off port cap 98 is within infusion-bag receptacle 44. A wall of infusion-bag receptacle 44 may be sufficiently flexible to allow manual manipulation of break-off port cap 98 while it is within infusion-bag receptacle 44. For other applications, break-off port cap 98 is broken off before inserting IV tubing port 34 into infusion-bag receptacle 44 (typically, IV tubing port 34 comprises a septum, as is known in the art).

As also shown in FIG. 2F, a volume of IV solution 94 is drawn from infusion bag 32 into syringe barrel 82 of syringe 80, which is sealingly coupled in fluid communication with syringe-interface end 54 of medication-preparation tubing 48, by withdrawing syringe handle 86 accessible from outside airtight enclosure 40. For example, IV solution 94 may comprise saline or another IV solution, such as a balanced IV solution, as is known in the art.

Figure 2G:
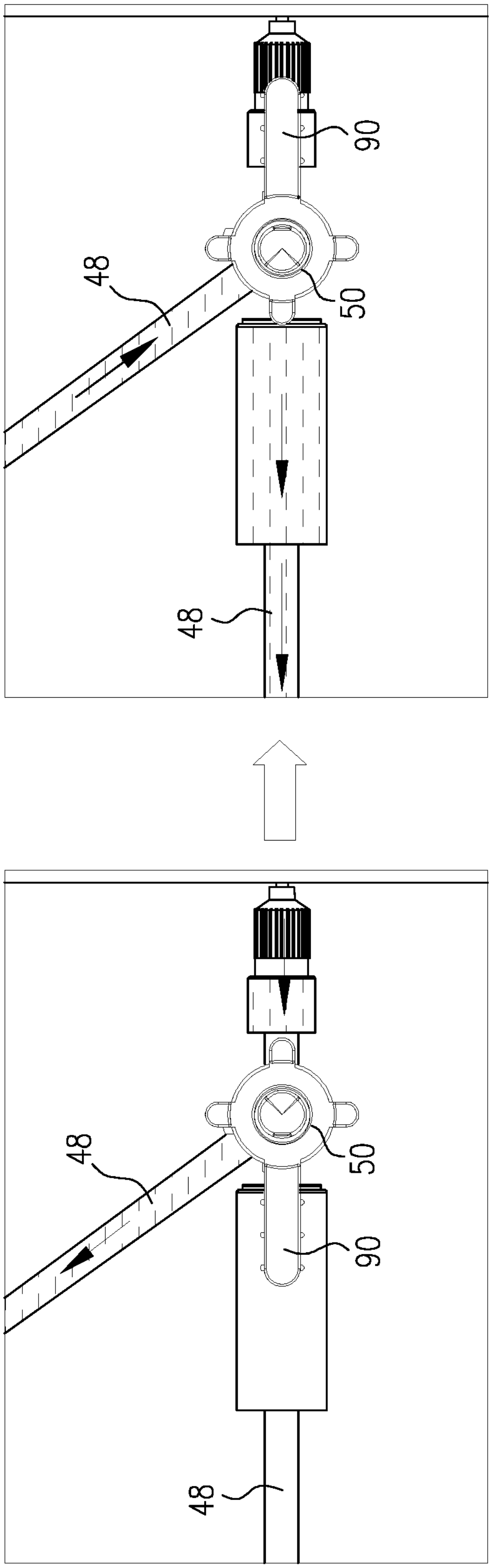

As shown in FIG. 2G and as described hereinabove with reference to FIG. 1, sterile closed system 20 further comprises one or more medication-preparation-tubing valves 50, which regulate flow between syringe-interface end 54, medication-vial-interface end 56, and medication-port-interface end 58 of medication-preparation tubing 48. Typically, the one or more medication-preparation-tubing valves 50 are configured to assume at least:

- a first state, shown in the left pane of FIG. 2G, in which the one or more medication-preparation-tubing valves 50 (a) allow flow between syringe-interface end 54 and medication-port-interface end 58 of medication-preparation tubing 48, and (b) block flow (i) between medication-vial-interface end 56 and medication-port-interface end 58 and (ii) between medication-vial-interface end 56 and syringe-interface end 54, and
- a second state, shown in the right pane of FIG. 2G, in which the one or more medication-preparation-tubing valves 50 (a) allow flow between syringe-interface end 54 and medication-vial-interface end 56, and (b) block flow (i) between medication-vial-interface end 56 and medication-port-interface end 58 and (ii) between syringe-interface end 54 and medication-port-interface end 58.

Typically, the volume of IV solution 94 is drawn from infusion bag 32 into syringe barrel 82 while the one or more medication-preparation-tubing valves 50 are in the first state. At this step of the method, the exact volume of IV solution 94 can be set by withdrawing an exact volume of IV solution 94 into syringe barrel 82, such as using conventional graduated marks on the barrel.

Figure 2H:
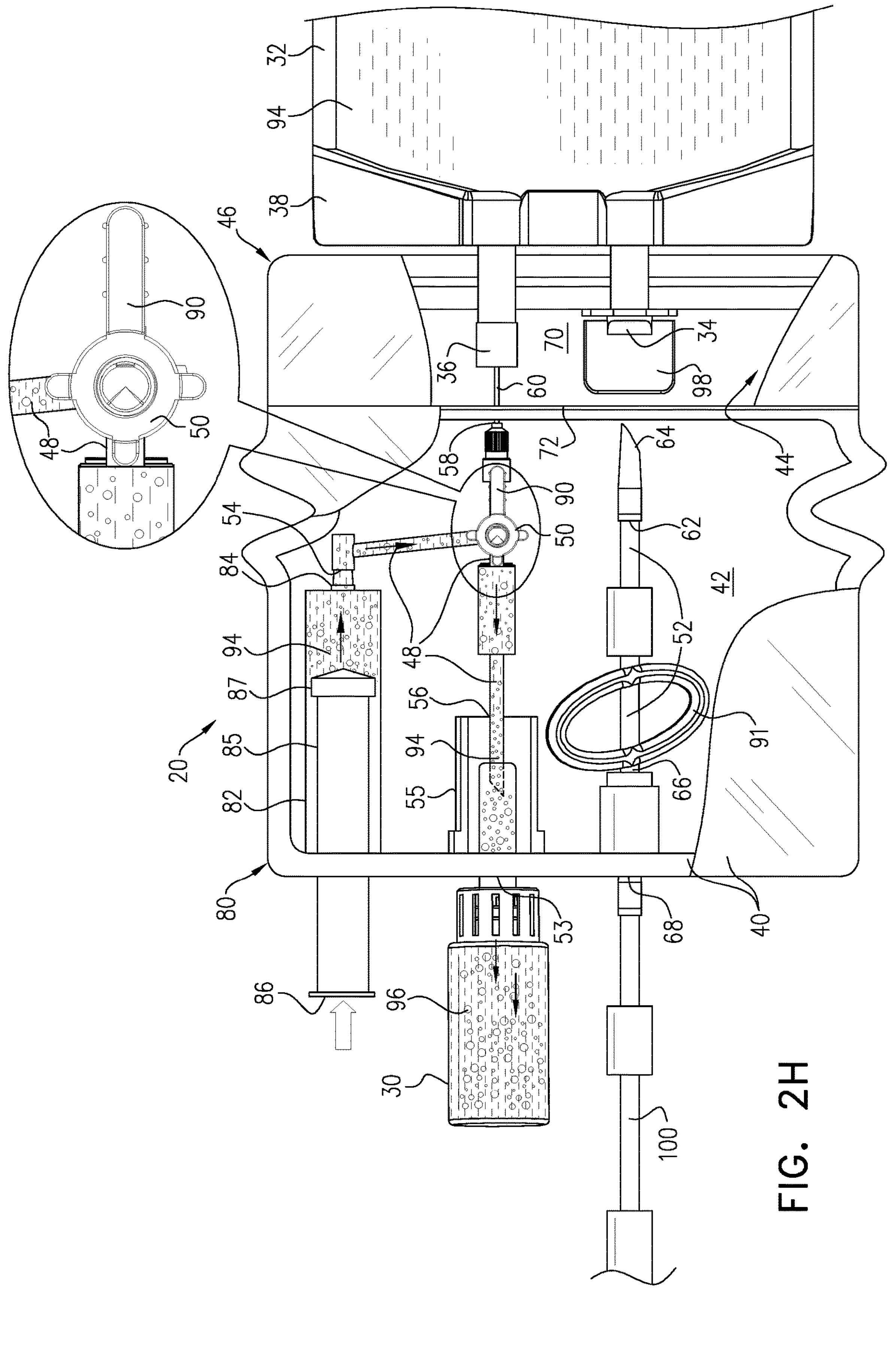

As shown in FIG. 2H, while syringe 80 remains sealingly coupled in fluid communication with syringe-interface end 54, the volume of IV solution 94 is transferred from syringe barrel 82 to medication vial 30 by pushing syringe handle 56. Typically, the volume of IV solution 94 is transferred from syringe barrel 82 to medication vial 30 while the one or more medication-preparation-tubing valves 50 are in the second state, after the one or more medication-preparation-tubing taps 90 have been used to transition the valves from the first state to the second state.

While medication vial 30 remains coupled to sterile closed system 20, medication vial 30 is agitated to mix the medication with the volume of IV solution 94 to produce a diluted medication 96. (The medication may dissolve in IV solution 94, or become suspended in IV solution 94, depending on the type of medication.)

Figure 2I:
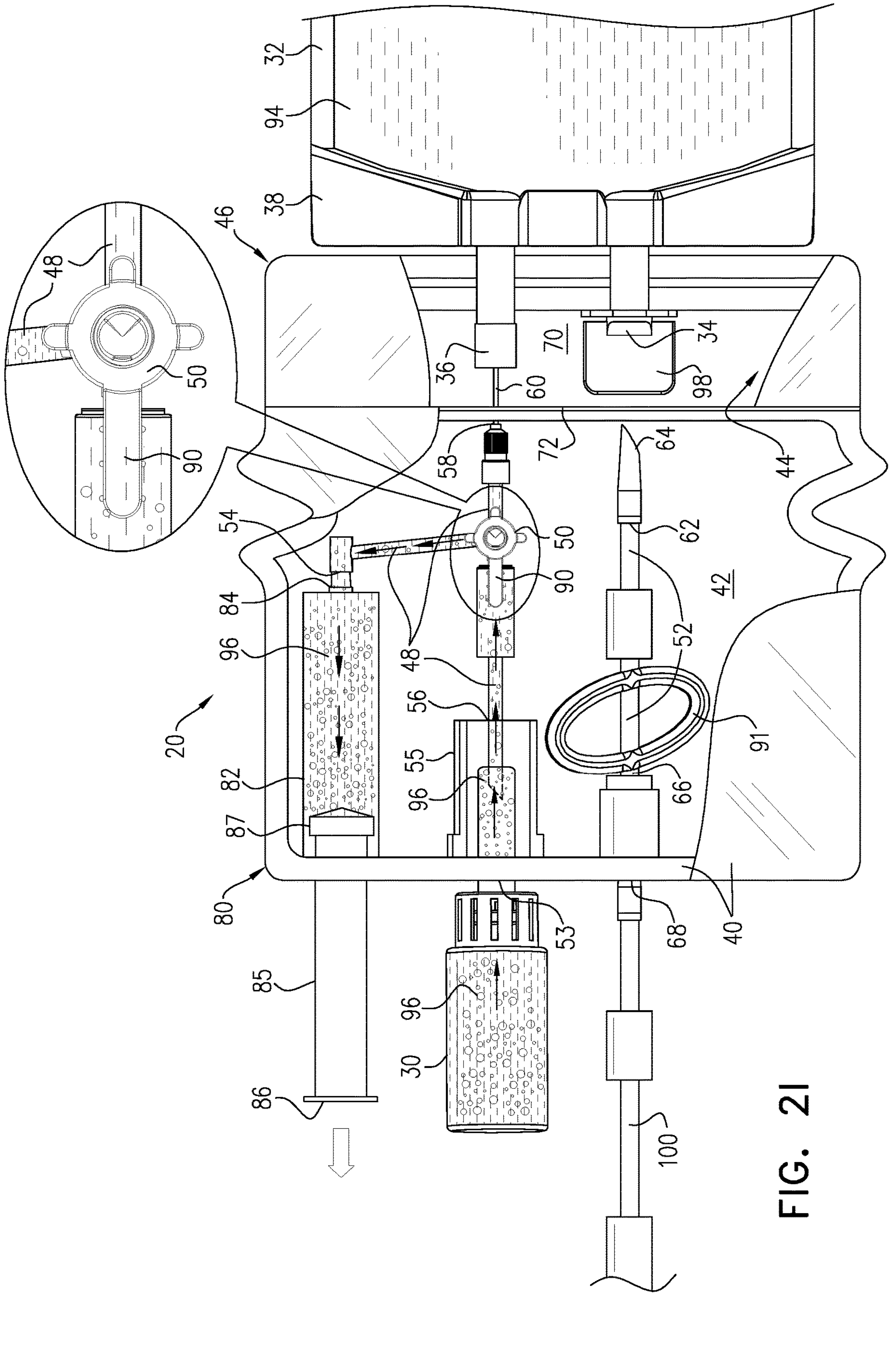

As shown in FIG. 2I, while medication vial 30 remains coupled to sterile closed system 20 and syringe 80 remains sealingly coupled in fluid communication with syringe-interface end 54, diluted medication 96 is transferred from medication vial 30 to syringe barrel 82 by withdrawing syringe handle 86. Typically, diluted medication 96 is transferred from medication vial 30 to syringe barrel 82 while the one or more medication-preparation-tubing valves 50 are in the second state. At this step of the method, the exact dose of diluted medication 96 can be set by withdrawing an exact volume of diluted medication 96 into syringe barrel 82, such as using conventional graduated marks on the barrel.

Figure 2J:
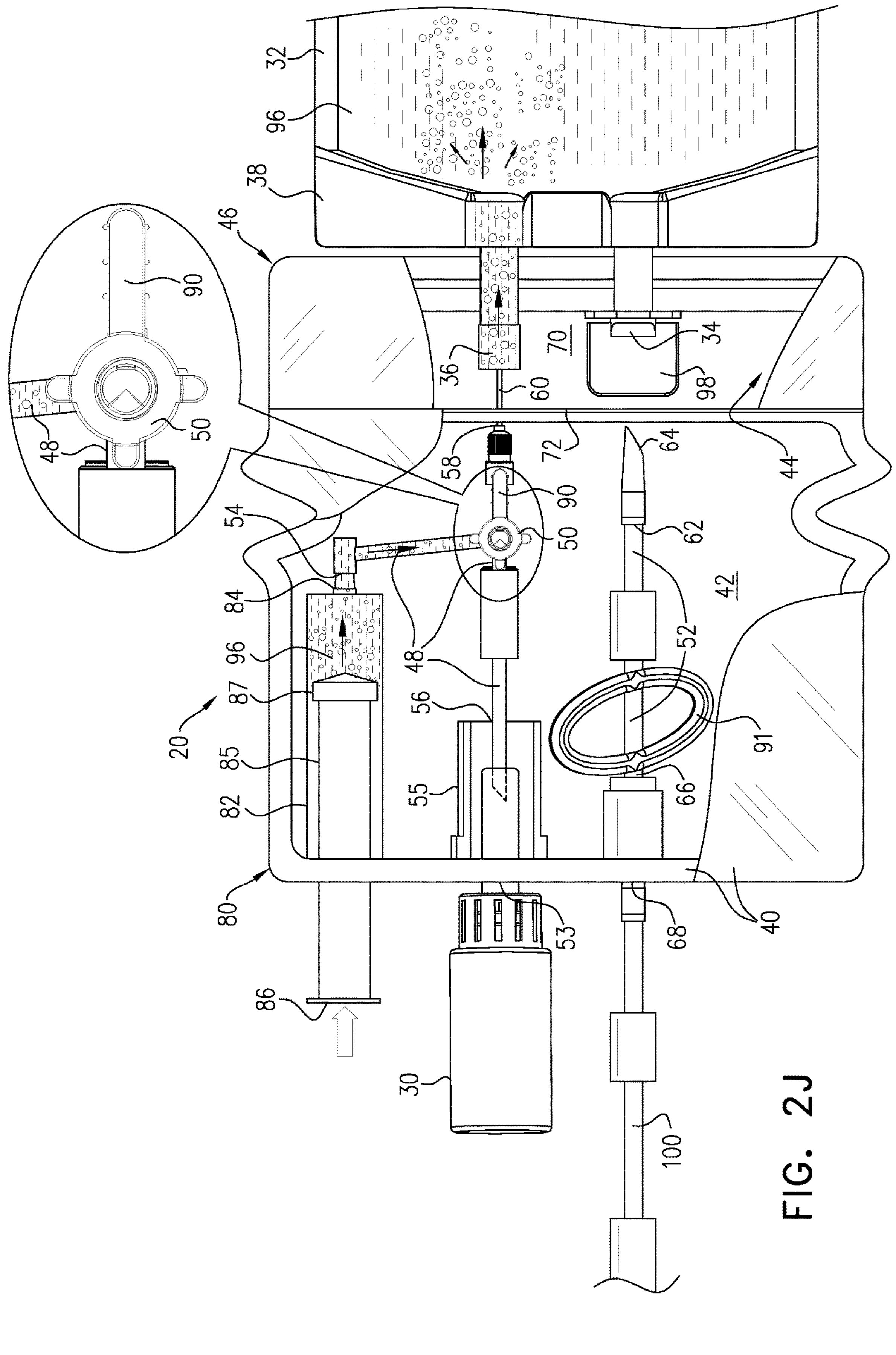
Figure 2K:
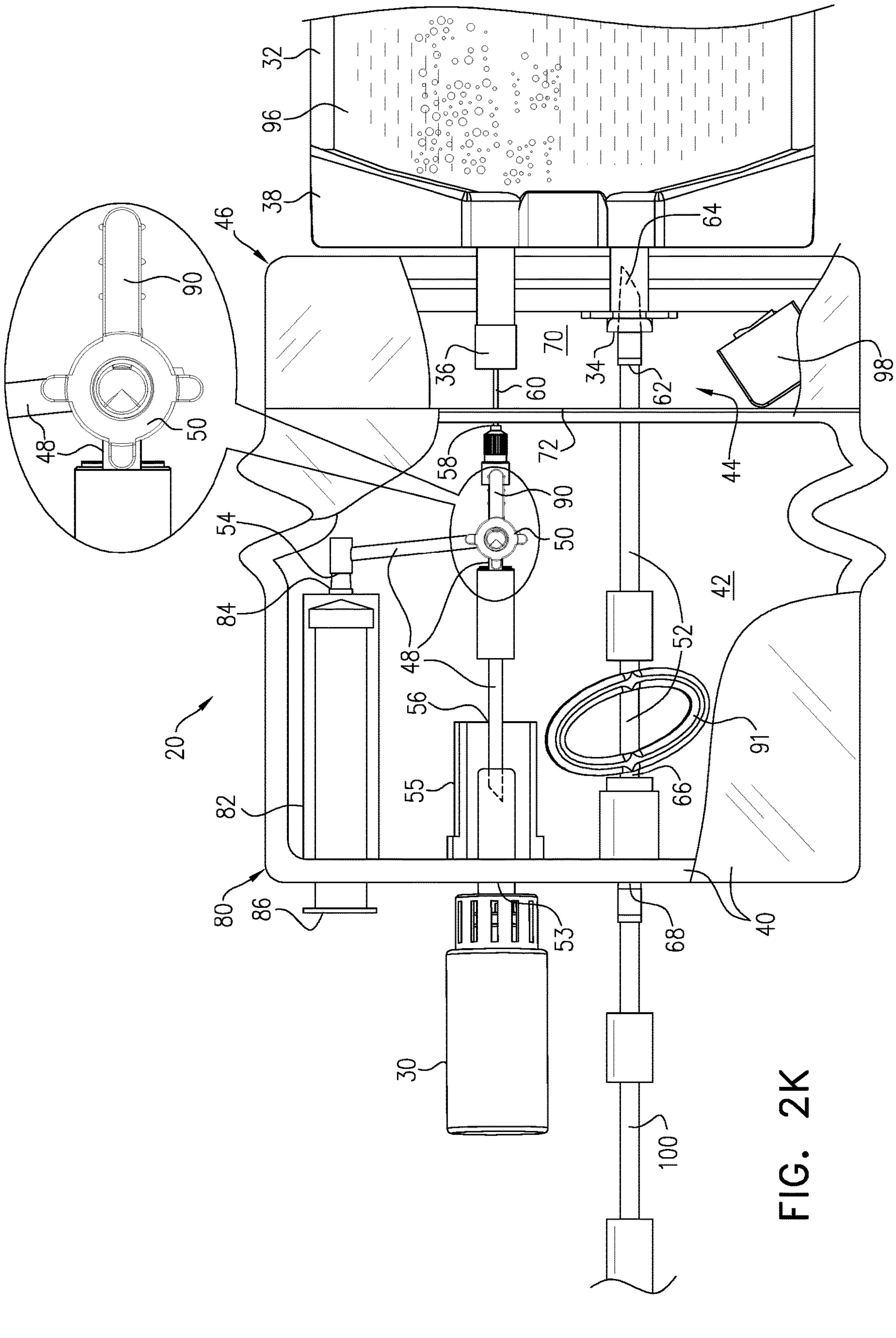

As shown in FIG. 2K, while syringe 80 remains sealingly coupled in fluid communication with syringe-interface end 54, diluted medication 96 is transferred from syringe barrel 82 to infusion bag 32 by pushing syringe handle 86. Typically, diluted medication 96 is transferred from syringe barrel 82 to infusion bag 32 while the one of more medication-preparation-tubing valves 50 are in the first state, after the one or more medication-preparation-tubing taps 90 have been used to transition the valves from the second state to the first state.

Typically, the first and the second states of the one or more medication-preparation-tubing valves 50 described hereinabove with reference to FIGS. 2F-K are set using the one or more medication-preparation-tubing taps 90 that are manipulable from outside airtight enclosure 40, as described hereinabove with reference to FIG. 1. Optionally, the first and the second states are set using exactly one medication-preparation-tubing tap 90 that is manipulable from outside airtight enclosure 40, such as described hereinbelow with reference to FIGS. 4A-B.

The medication preparation performed at the steps of the method described with reference to FIGS. 2F-K are performed in the sterile, closed environment provided by sterile closed system 20, which is impermeable to the entry of air or any other contamination from the environment, and to the exit of drug vapor, such as cytotoxic drug vapor or antibiotic vapor, to the environment outside the system.

As shown in FIG. 2J, while infusion-bag seal 46 is in the sealing state, IV-tubing-port-interface spike 64 is sealingly coupled to IV tubing port 34 of infusion bag 32 without breaking the airtight seal between infusion-bag seal 46 and the respective external surfaces of medication port 36 and IV tubing port 34 of infusion bag 32. As described hereinabove with reference to FIG. 1, airtight enclosure 40 is typically configured to allow IV-tubing-port-interface spike 64 to move with respect to IV tubing port 34 of infusion bag 32 when infusion-bag seal 46 is in the sealing state. Typically, mechanical action external to the system is used to sealingly couple IV-tubing-port-interface spike 64 to IV tubing port 34 of infusion bag 32.

For some applications, the method further comprises sealingly coupling IV tubing 100 to medication-delivery port 68. For some applications, medication-delivery port 68 comprises a spike port adapter, as is known the art and commercially available, for example, the Equashield® Spike Adaptor (Equashield LLC, Port Washington, NY, USA), the Tevadaptor® Spike Port Adaptor (Teva Medical Ltd., Kiryat Shmona, Israel), or the Infusion Adapter C100, BD Phaseal (Medisca Inc., Plattsburgh, NY, USA).

This coupling may be performed at any point during the method while infusion-bag seal 46 is in the sealing state, such as shown in FIGS. 2C-L, in which case this coupling is typically performed while medication vial 30 remains coupled to sterile closed system 20. Alternatively, IV tubing 100 is sealingly coupled to medication-delivery port 68 of medication-delivery tubing 52 while infusion-bag seal 46 is still in the non-sealing state before being transitioned to the sealing state, as shown in FIGS. 2A-B. In either case, the system prevents any possible dripping of the medication out of the system into the external environment, or contamination of the drug from the external environment.

FIG. 2K shows sterile closed system 20 upon the completion of the method described with reference to FIGS. 2A-K.

In some applications of the present invention, sterile closed system 20 does not comprise medication-delivery port 68. Instead, the system comprises tubing having two contiguous longitudinal segments, one of which serves as medication-delivery tubing 52 and the other of which serves as IV tubing 100. The tubing passes through the wall of airtight enclosure 40 with an airtight seal. This, in this configuration, sterile closed system 20 comprises IV tubing 100, which is provided as an integral part of the system. This configuration obviates the need for the healthcare worker to couple separate IV tubing 100 to medication-delivery port 68.

Figure 2L:
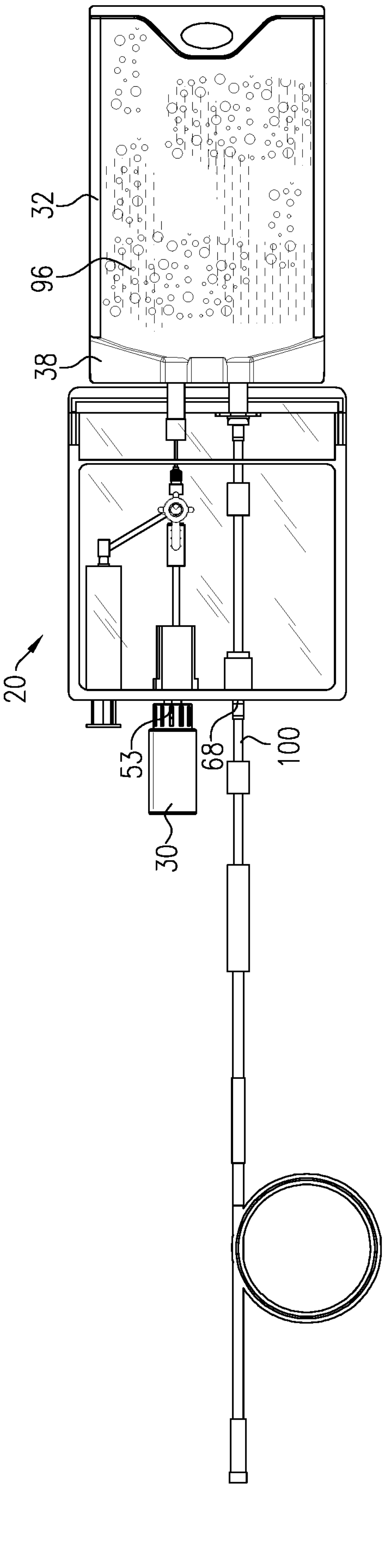

Typically, the method further comprises performing an infusion via IV tubing 100, as shown in FIG. 2L. Typically, an entirety of the infusion is performed while medication vial 30 remains coupled to sterile closed system 20. This may prevent leakage and contamination. In addition, the original labeling of medication vial 30 remains coupled to and associate with sterile closed system 20, such that healthcare workers can confirm the correct medication and correct patient at all stages of the process, thereby preventing possible errors in administration. Sterile closed system 20, including the external elements attached thereto during use, can be disposed of in a single piece after use, without disconnection of any elements, such as medication vial 30 or infusion bag 32.

For some applications, the method does not comprise attaching to or detaching from sterile closed system 20 any elements other than infusion bag 32, medication vial 30, and IV tubing 100.

Figure 3:
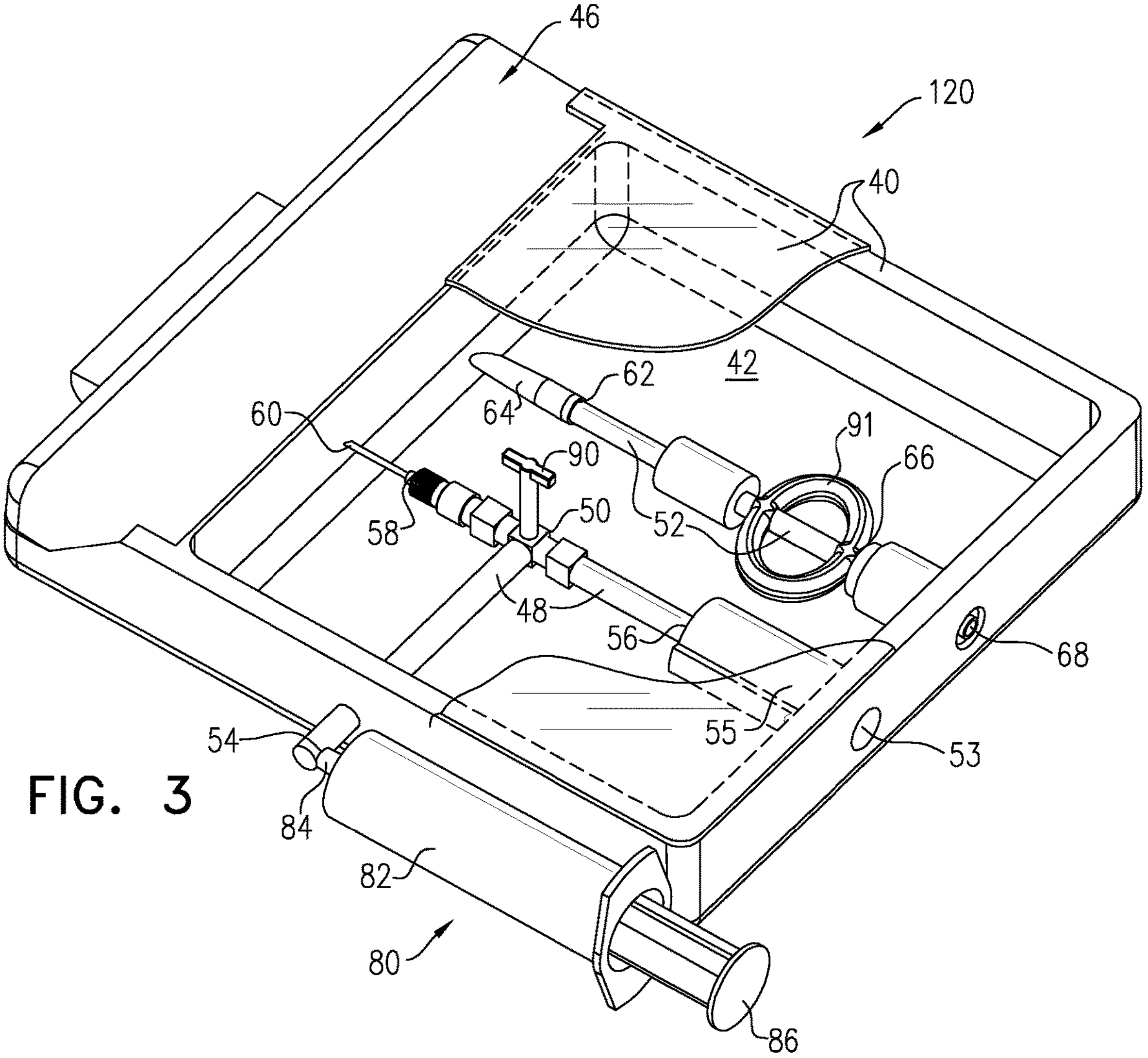
FIG. 3 is a schematic illustration of another sterile closed system, in accordance with an application of the present invention.

Reference is now made to FIG. 3, which is a schematic illustration of a sterile closed system 120, in accordance with an application of the present invention. Other than as described below, sterile closed system 120 is identical to sterile closed system 20, described hereinabove with reference to FIGS. 1 and 2A-L, and like reference numeral refer to like parts. In this configuration, syringe barrel 82 is located at least partially (such as mostly, e.g., entirely) outside enclosure interior 42. This may allow the use of a smaller airtight enclosure 40.

For some applications, hollow tip 84 of syringe barrel 82 is permanently sealingly connected in fluid communication with syringe-interface end 54 of medication-preparation tubing 48. For these applications, sterile closed system 120 comprises syringe 80.

For other applications, syringe 80 is not an element of sterile closed system 120, and is coupled to the system by a healthcare worker during use. Typically, the syringe is conventional. This may provide greater flexibility to select an appropriate volume for the particular medication, such as a syringe barrel 82 having a volume of 1-60 ml.

For some applications, syringe 80 includes a syringe screw-on fitting (e.g., a Luer-Lock interface). Syringe-interface end 54 of medication-preparation tubing 48 comprises a syringe-interface fitting, which is configured to be sealingly coupled to the syringe screw-on fitting so as to couple syringe 80 in fluid communication with syringe-interface end 54.

For other applications, syringe 80 includes a syringe needle, and syringe-interface end 54 of medication-preparation tubing 48 comprises a septum, which is puncturable by the syringe needle in order to sealingly couple syringe 80 in fluid communication with syringe-interface end 54.

Reference is now made to FIGS. 4A-B, which are schematic illustrations of a medication-preparation-tubing valve 250 and a medication-preparation-tubing tap 290, in accordance with an application of the present invention. In this configuration, sterile closed system 20 comprises exactly one medication-preparation-tubing valve 250, which regulates flow between syringe-interface end 54, medication-vial-interface end 56, and medication-port-interface end 58 of medication-preparation tubing 48. In addition, in this configuration, sterile closed system 20 comprises exactly one medication-preparation-tubing tap 290, which is configured to set the two or more states of medication-preparation-tubing valve 250. Medication-preparation-tubing valve 250 and medication-preparation-tubing tap 290 are implementations of medication-preparation-tubing valve 50 and a medication-preparation-tubing tap 90, respectively, described hereinabove with reference to FIGS. 1 and 2A-L.

As described hereinabove with reference to FIG. 2F regarding medication-preparation-tubing valve 50, medication-preparation-tubing valve 250 is configured to assume at least:

- the first state, shown in FIG. 4A, in which medication-preparation-tubing valves 250 (a) allows flow between syringe-interface end 54 and medication-port-interface end 58 of medication-preparation tubing 48, and (b) blocks flow (i) between medication-vial-interface end 56 and medication-port-interface end 58 and (ii) between medication-vial-interface end 56 and syringe-interface end 54, and
- the second state, shown in FIG. 4B, in which medication-preparation-tubing valves 250 (a) allows flow between syringe-interface end 54 and medication-vial-interface end 56, and (b) blocks flow (i) between medication-vial-interface end 56 and medication-port-interface end 58 and (ii) between syringe-interface end 54 and medication-port-interface end 58.

Medication-preparation-tubing tap 290 is configured to set the two or more states of medication-preparation-tubing valve 250, and is manipulable from outside airtight enclosure 40. For example, rotation of medication-preparation-tubing tap 290 by 180 degrees (such as shown), or by 90 degrees (configuration not shown), may set the two or more states of medication preparation-tubing valve 250.

Reference is now made to FIGS. 5A-B and 6A-B, which are schematic illustrations of a glass ampoule adapter 300 for use with a glass ampoule 302, in accordance with an application of the present invention.

Figure 7A:
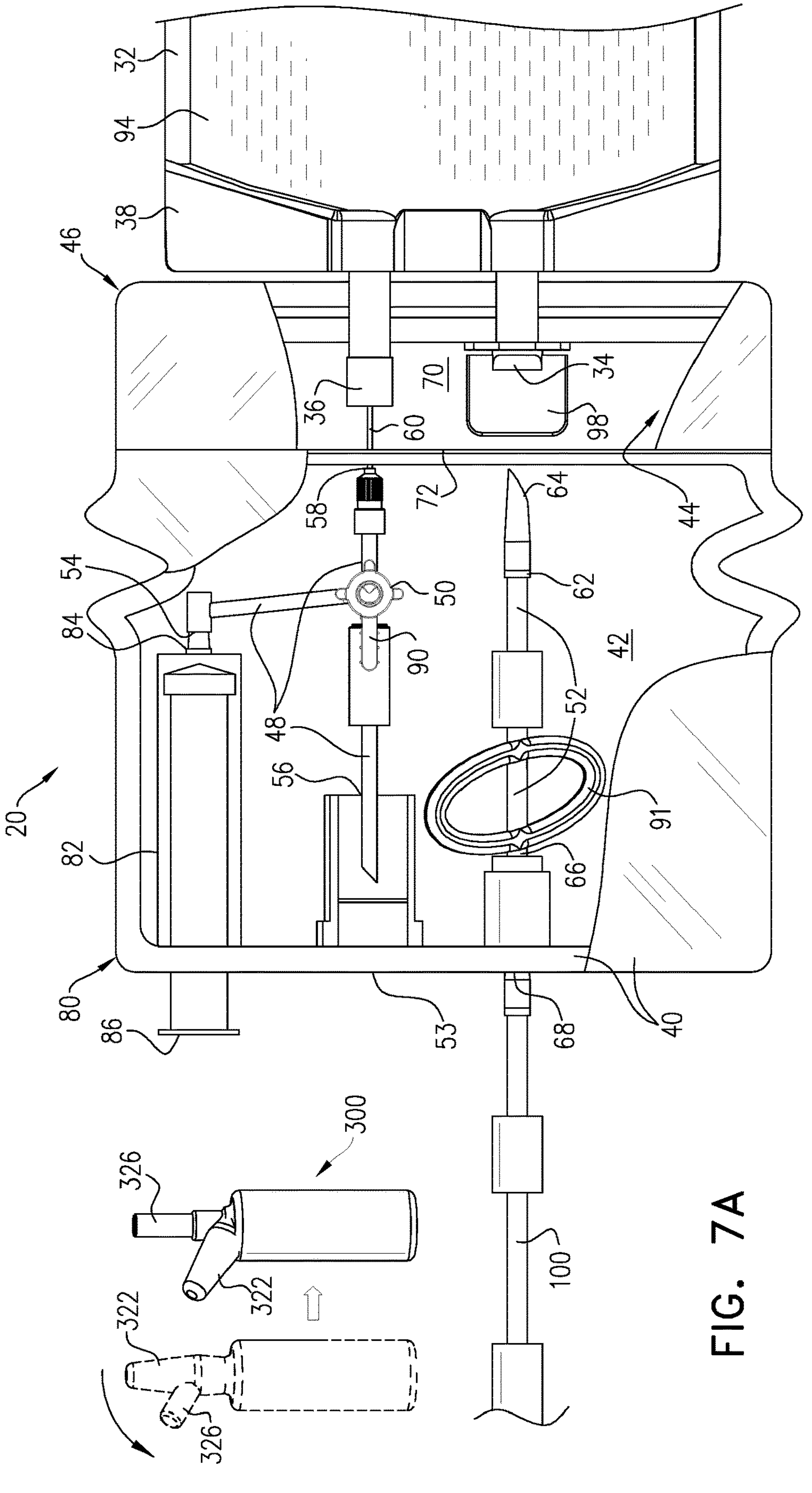
FIGS. 7A-C are schematic illustrations of the use of the glass ampoule adapter of FIGS. 5A-B and 6A-B with the sterile closed system of FIG. 1, in accordance with an application of the present invention.
Figure 7B:
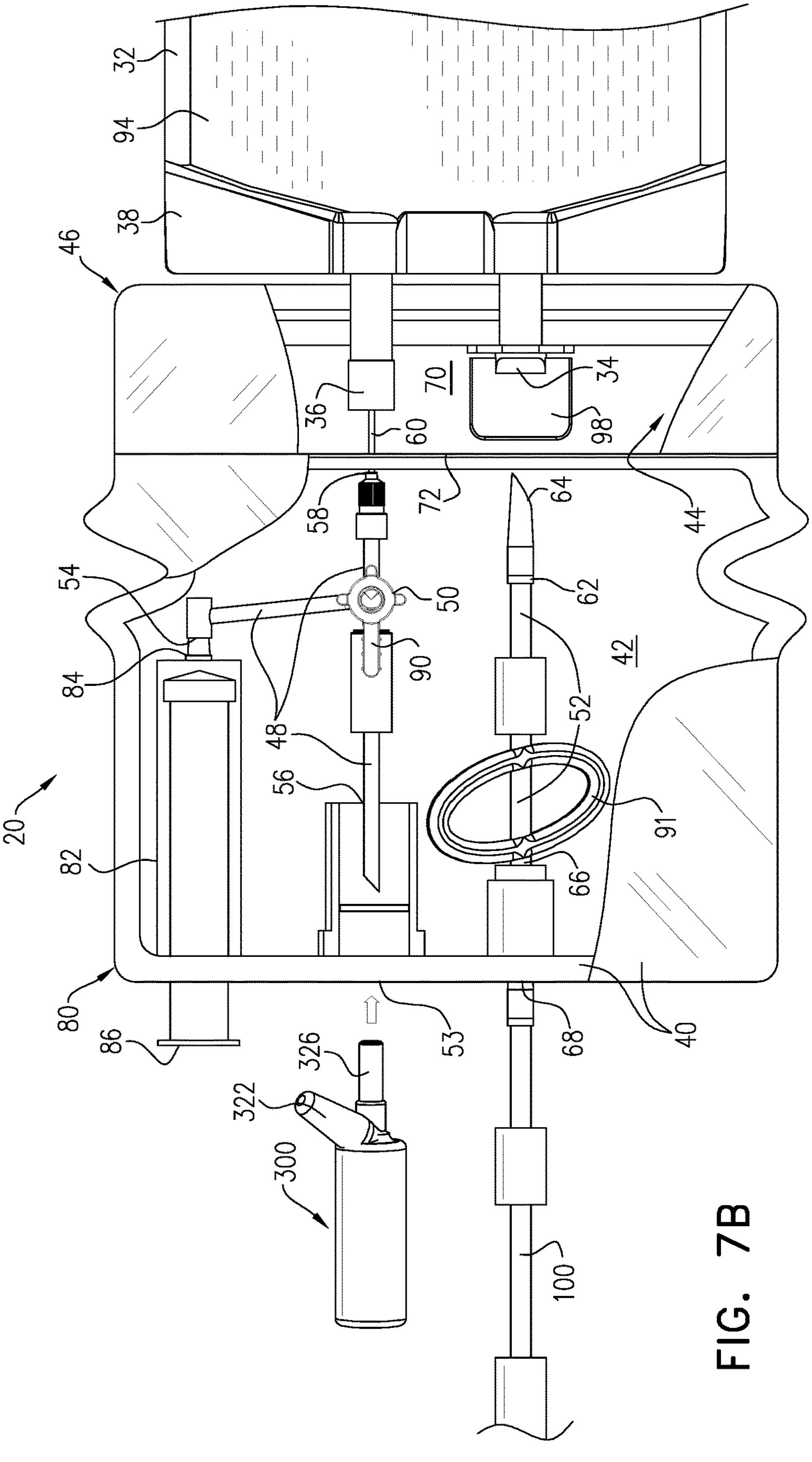
Figure 7C:
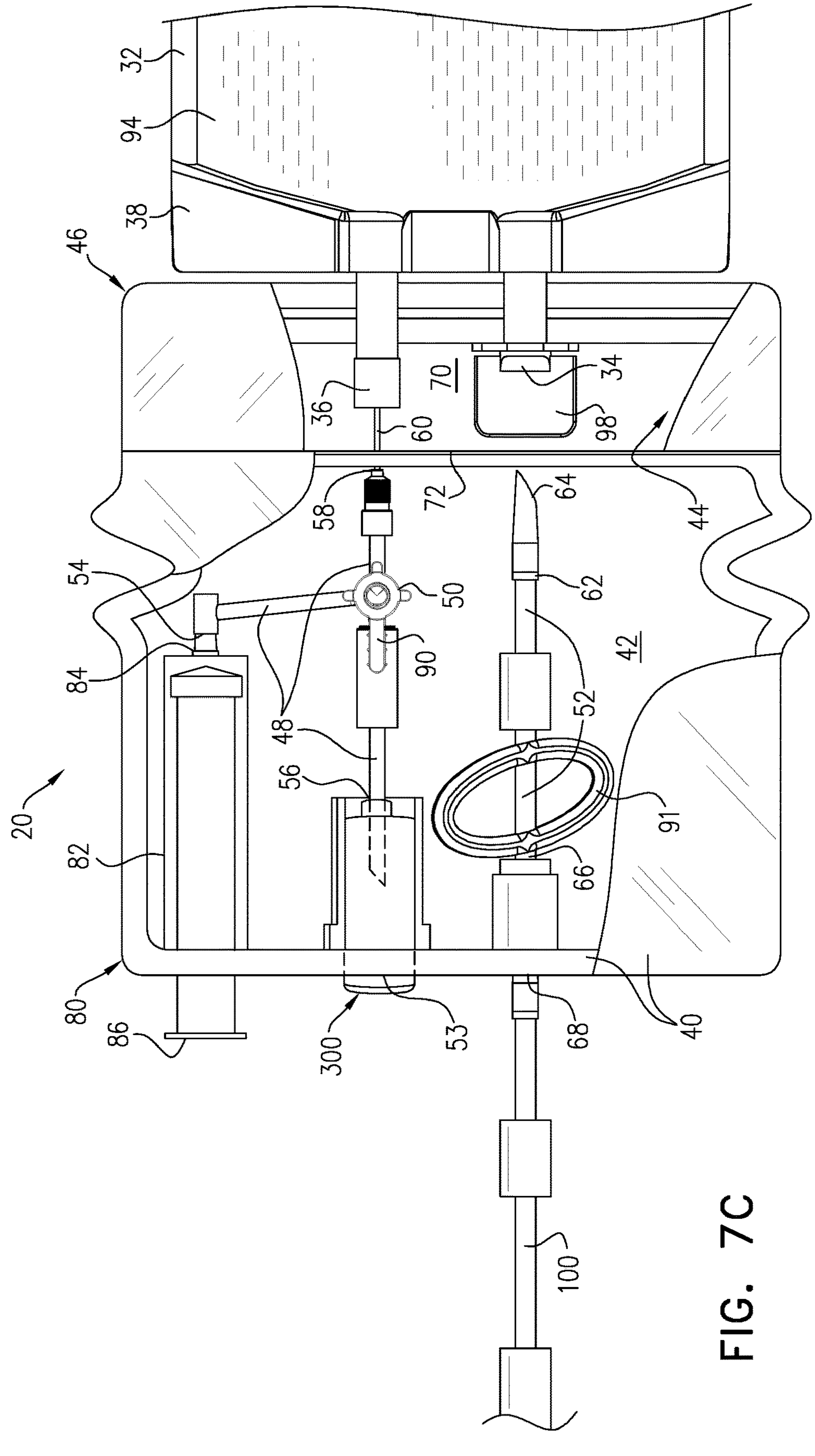

Reference is also made to FIGS. 7A-C, which are schematic illustrations of the use of glass ampoule adapter 300 with sterile closed system 20, in accordance with an application of the present invention. Glass ampoule adapter 300 may optionally be used with sterile closed system 20 or 120 in applications in which medication vial 30 is a glass ampoule 302, and in which medication-vial-interface end 56 is configured to be sealingly coupled to glass ampoule 302. Alternatively, glass ampoule adapter 300 may be used with any medication delivery system which requires sterile coupling of a glass ampoule 302 (configuration not shown), Regardless of its use, glass ampoule 302 is typically not an element of the invention, but rather a conventional glass ampoule that is used with glass ampoule adapter 300.

The use of glass ampoule adapter 300 may help prevent injury to the healthcare worker that is preparing the medication contained in the glass ampoule. As is known in the art, "The sharp, jagged edges formed when the ampoule neck breaks incompletely pose a serious danger to medical professionals" (Stoker R, "Preventing Injuries from Glass Ampoule Shards," Managing Infection Control, October 2009, pp. 45-47). The use of glass ampoule adapter 300 may alternatively or additionally reduce the risk of leakage of toxic medication into the atmosphere.

Glass ampoule adapter 300 comprises:

- a flexible proximal elongate body enclosure 310, which has an elongate interior 312 shaped so as to accept and enclose a body 314 of glass ampoule 302, and which is shaped so as to define an insertion opening 316 through which glass ampoule body 314 is insertable into elongate interior 312;
- a flexible neck enclosure 318, which is shaped so as to make an airtight seal with a neck 320 of glass ampoule 302 when glass ampoule body 314 is inserted into elongate interior 312;
- a flexible distal elongate tip enclosure 322, which is sealingly coupled to proximal elongate body enclosure 310 by flexible neck enclosure 318, and which is shaped so as to accept and enclose a up 324 of glass ampoule 302 when glass ampoule body 314 is inserted into elongate interior 312; and
- a flexible septum 326, which extends radially outward from an external lateral surface 328 of distal elongate tip enclosure 322.

For some applications, flexible septum 326 is shaped similarly to a conventional septum of a Luer lock connector, cut in the shape of a cross; pressing in causes the septum to open and allow a needle/syringe penetration of a syringe to be sucked out of the open ampoule.

For some applications, flexible proximal elongate body enclosure 310 is shaped so as to define insertion opening 316 through and end of proximal elongate body enclosure 310 opposite the end at which proximal elongate body enclosure 310 is coupled to flexible neck enclosure 318.

Figure 5A:
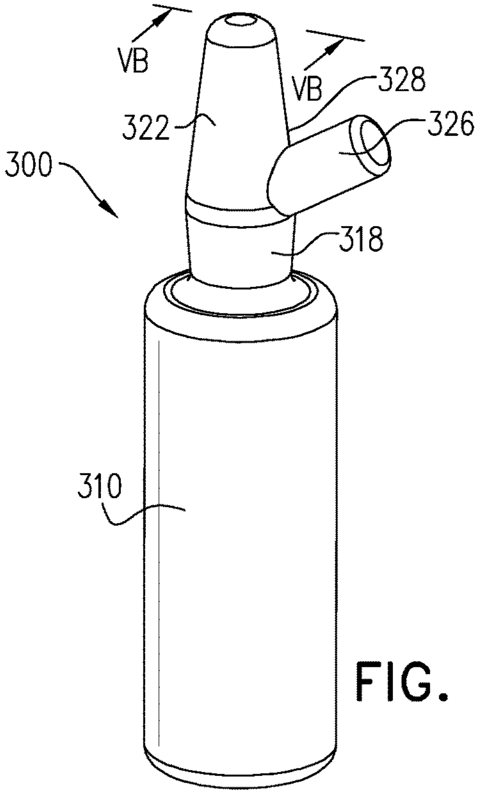
FIGS. 5A-B and 6A-B are schematic Illustrations of a glass ampoule adapter for use with a glass ampoule, in accordance with an application of the present invention.
Figure 5B:
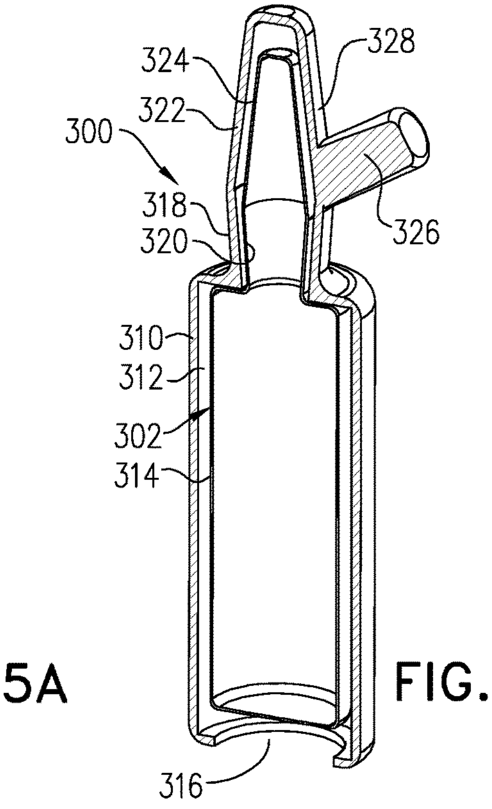
Figure 6A:
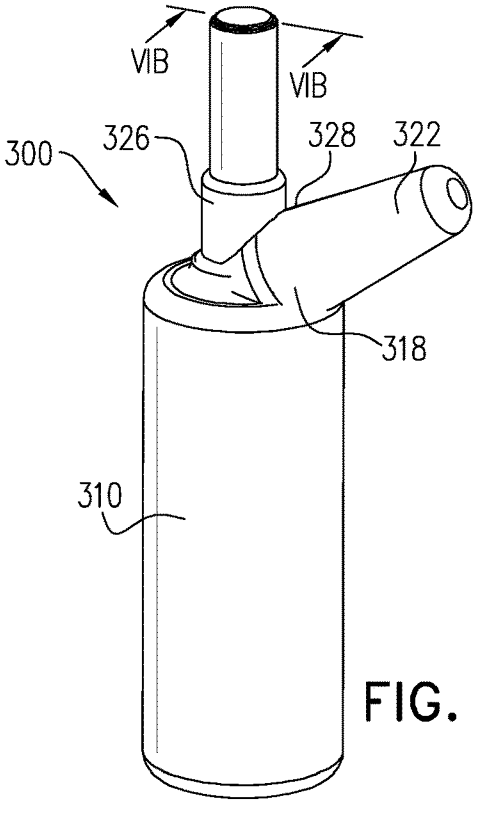
Figure 6B:
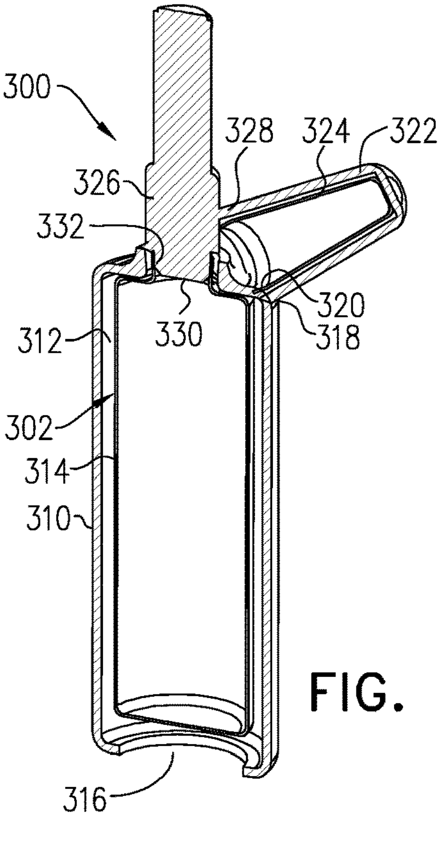

Glass ampoule adapter 300 is configured such that, when glass ampoule 302 is within glass ampoule adapter 300, such as shown FIG. 5B, sideways movement of distal elongate tip enclosure 322:

- deflects glass ampoule tip 324 sideways with respect to glass ampoule body 314, thereby breaking glass ampoule neck 320 and snapping glass ampoule tip 324 off glass ampoule body 314 to create a distal opening 330 in glass ampoule body 314, and
- aligns flexible septum 326 with glass ampoule body 314 and forms a seal 332 with broken glass ampoule neck 320, thereby sealing distal opening 330 of glass ampoule body 314.

For some applications, after the sideways movement of distal elongate tip enclosure 322, as shown in FIGS. 5B and 7A, the contents of glass ampoule body 314 can then be sealingly coupled in fluid communication with medication-vial-interface end 56, such by inserting a needle of medication-vial-interface end 56 through flexible septum 326, such as shown in the transition between FIGS. 7B and 7C. Glass ampoule body 314 can alternatively be sealing coupled in fluid communication with another interface of another medication delivery system, such as by inserting a needle of the system through the septum.

Typically, glass ampoule adapter 300 comprises an elastic material. For example, the material may comprise elastic/latex rubber.

For some applications, flexible proximal elongate body enclosure 310, flexible neck enclosure 318, and flexible distal elongate tip enclosure 322 are integrally formed from a single piece of flexible material, e.g., by injection molding. For example, the material may comprise silicone, rubber, or polypropylene glycol. Optionally, flexible septum 326 is also integrally formed from the same piece of flexible material as the other components.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A sterile closed system for sterile connection to a medication vial and to an infusion bag having an IV tubing port and a medication port extending from a bottom region of the infusion bag, the sterile closed system comprising:

an airtight enclosure, shaped so as to define an enclosure interior;

an infusion-bag receptacle;

an infusion-bag seal, which is configured, when in a sealing state, to make an airtight seal with respective external surfaces of the medication port and the IV tubing port of the infusion bag, when the medication port and the IV tubing port are inserted at least partially into the infusion-bag receptacle;

a medication-vial port, which is accessible from outside the airtight enclosure, and which is configured to be sealingly coupled to the medication vial so as to couple the medication vial to the sterile closed system;

a medication-port-interface needle, disposed within the enclosure interior;

an IV-tubing-port-interface spike, disposed within the enclosure interior;

medication-preparation tubing, which is shaped so as to define (a) a syringe-interface end, (b) a medication-vial-interface end, which is in fluid communication with medication-vial port, and (c) a medication-port-interface end, which is disposed within the enclosure interior, and which is in fluid communication with the medication-port-interface needle;

one or more medication-preparation-tubing valves, which regulate flow between the syringe-interface end, the medication-vial-interface end, and the medication-port-interface end of the medication-preparation tubing; and medication-delivery tubing, which is shaped so as to define an IV-tubing-port-interface end, which is in fluid communication with the IV-tubing-port-interface spike, wherein the sterile closed system is configured such that, when the infusion-bag seal is in the sealing state:

the medication-port-interface needle is sealingly couplable to the medication port of the infusion bag without breaking the airtight seal between the infusion-bag seal and the respective external surfaces of the medication port and the IV tubing port of the infusion bag, and the IV-tubing-port-interface spike is sealingly couplable to the IV tubing port of the infusion bag without breaking the airtight seal between the infusion-bag seal and the respective external surfaces of the medication port and the IV tubing port of the infusion bag.

2. The sterile closed system according to claim 1, wherein the medication vial is a glass ampoule, and wherein the medication-vial-interface end is configured to be sealingly coupled to the glass ampoule.

3. The sterile closed system according to claim 1, wherein the sterile closed system does not comprise any elements that are attachable or detachable during ordinary use.

4. The sterile closed system according to claim 1, wherein the airtight enclosure is configured to allow the medication-port-interface needle and the IV-tubing-port-interface spike to move with respect to the medication port of the infusion bag and the IV tubing port of the infusion bag, respectively, when the infusion-bag seal is in the sealing state.

5. The sterile closed system according to claim 1, wherein the sterile closed system comprises exactly one medication-preparation-tubing valve, which regulates flow between the syringe-interface end, the medication-vial-interface end, and the medication-port-interface end of the medication-preparation tubing.

6. The sterile closed system according to claim 1, wherein the one or more medication-preparation-tubing valves are configured to assume at least:

a first state, in which the one or more medication-preparation-tubing valves (a) allow flow between the syringe-interface end and the medication-port-interface end of the medication-preparation tubing, and (b) block flow (i) between the medication-vial-interface end and the medication-port-interface end and (ii) between the medication-vial-interface end and the syringe-interface end, and a second state, in which the one or more medication-preparation-tubing valves (a) allow flow between the syringe-interface end and the medication-vial-interface end, and (b) block flow (i) between the medication-vial-interface end and the medication-port-interface end and (ii) between the syringe-interface end and the medication-port-interface end.

7. The sterile closed system according to claim 1, wherein the infusion-bag receptacle is shaped so as to define an infusion-bag receptacle interior, wherein the enclosure interior and the infusion-bag receptacle interior are shaped so as to define a common wall that separates the enclosure interior and the infusion-bag receptacle interior from each other, and wherein the sterile closed system is configured such that, when the infusion-bag seal is in the sealing state:

the medication-port-interface needle is sealingly couplable to the medication port of the infusion bag by penetrating the common wall without breaking the airtight seal between the infusion-bag seal and the respective external surfaces of the medication port and the IV tubing port of the infusion bag, and the IV-tubing-port-interface spike is sealingly couplable to the IV tubing port of the infusion bag by penetrating the common wall without breaking the airtight seal between the infusion-bag seal and the respective external surfaces of the medication port and the IV tubing port of the infusion bag.

8. The sterile closed system according to claim 7, wherein the common wall comprises a septum, and wherein the sterile closed system is configured such that, when the infusion-bag seal is in the sealing state, the medication-port-interface needle is sealingly couplable to the medication port of the infusion bag by penetrating the septum of the common wall without breaking the airtight seal between the infusion-bag seal and the respective external surfaces of the medication port and the IV tubing port of the infusion bag.

9. The sterile closed system according to claim 7, wherein the common wall comprises a septum, and wherein the sterile closed system is configured such that, when the infusion-bag seal is in the sealing state, the IV-tubing-port-interface spike is sealingly couplable to the IV tubing port of the infusion bag by penetrating the septum of the common wall without breaking the airtight seal between the infusion-bag seal and the respective external surfaces of the medication port and the IV tubing port of the infusion bag.

10. The sterile closed system according to claim 1, for use with a syringe having a syringe needle, wherein the syringe-interface end of the medication-preparation tubing comprises a septum, which is puncturable by the syringe needle in order to sealingly couple the syringe in fluid communication with the syringe-interface end.

11. The sterile closed system according to claim 1, further comprising one or more medication-preparation-tubing taps, which are configured to set two or more states of the one or more medication-preparation-tubing valves, and which are manipulable from outside the airtight enclosure.

12. A method comprising:

at least partially inserting a medication port and an IV tubing port that extend from a bottom region of an infusion bag into an infusion-bag receptacle of a sterile closed system, such that an infusion-bag seal of the sterile closed system, when in a sealing state, makes an airtight seal with respective external surfaces of the medication port and the IV tubing port of the infusion bag within the infusion-bag receptacle, wherein the sterile closed system further comprises:

an airtight enclosure, shaped so as to define an enclosure interior;

a medication-vial port, which is accessible from outside the airtight enclosure;

a medication-port-interface needle, disposed within the enclosure interior;

an IV-tubing-port-interface spike, disposed within the enclosure interior;

medication-preparation tubing, which is shaped so as to define (a) a syringe-interface end, (b) a medication-vial-interface end, which in fluid communication with the medication-vial port, and (c) a medication-port-interface end, which (i) is disposed within the enclosure interior, and (ii) which is in fluid communication with the medication-port-interface needle; and medication-delivery tubing, which is shaped so as to define an IV-tubing-port-interface end, which is in fluid communication with the IV-tubing-port-interface spike;

sealingly coupling the medication-vial port to a medication vial containing a medication, so as to couple the medication vial to the sterile closed system;

while the infusion-bag seal is in the sealing state, sealingly coupling the medication-port-interface needle to the medication port of the infusion bag without breaking the airtight seal between the infusion-bag seal and the respective external surfaces of the medication port and the IV tubing port of the infusion bag;

drawing a volume of IV solution from the infusion bag into a syringe barrel of a syringe sealingly coupled in fluid communication with the syringe-interface end of the medication-preparation tubing, by withdrawing a syringe handle accessible from outside the airtight enclosure;

while the syringe remains sealingly coupled in fluid communication with the syringe-interface end, transferring the volume of the IV solution from the syringe barrel to the medication vial by pushing the syringe handle;

while the medication vial remains coupled to the sterile closed system, agitating the medication vial to mix the medication with the volume of the IV solution to produce a diluted medication;

while the medication vial remains coupled to the sterile closed system and the syringe remains sealingly coupled in fluid communication with the syringe-interface end, transferring the diluted medication from the medication vial to the syringe barrel by withdrawing the syringe handle;

while the syringe remains sealingly coupled in fluid communication with the syringe-interface end, transferring the diluted medication from the syringe barrel to the infusion bag by pushing the syringe handle; and while the infusion-bag seal is in the sealing state, sealingly coupling the IV-tubing-port-interface spike to the IV tubing port of the infusion bag without breaking the airtight seal between the infusion-bag seal and the respective external surfaces of the medication port and the IV tubing port of the infusion bag.

13. The method according to claim 12, wherein the method does not comprise attaching to or detaching from the sterile closed system any elements other than the infusion bag and the medication vial.

14. The method according to claim 12, wherein the airtight enclosure is configured to allow the medication-port-interface needle and the IV-tubing-port-interface spike to move with respect to the medication port of the infusion bag and the IV tubing port of the infusion bag, respectively, when the infusion-bag seal is in the sealing state.

15. The method according to claim 12, wherein the sterile closed system further comprises one or more medication-preparation-tubing valves, which regulate flow between the syringe-interface end, the medication-vial-interface end, and the medication-port-interface end of the medication-preparation tubing, wherein drawing the volume of the IV solution from the infusion bag into the syringe barrel comprises drawing the volume of the IV solution from the infusion bag into the syringe barrel while the one or more medication-preparation-tubing valves are in a first state, in which the one or more medication-preparation-tubing valves (a) allow flow between the syringe-interface end and the medication-port-interface end of the medication-preparation tubing, and (b) block flow (i) between the medication-vial-interface end and the medication-port-interface end and (ii) between the medication-vial-interface end and the syringe-interface end, wherein transferring the volume of the IV solution from the syringe barrel to the medication vial comprises transferring the volume of the IV solution from the syringe barrel to the medication vial while the one or more medication-preparation-tubing valves are in a second state, in which the one or more medicationpreparation-tubing valves (a) allow flow between the syringe-interface end and the medication-vial-interface end, and (b) block flow (i) between the medication-vial-interface end and the medication-port-interface end and (ii) between the syringe-interface end and the medication-port-interface end, wherein transferring the diluted medication from the medication vial to the syringe barrel comprises transferring the diluted medication from the medication vial to the syringe barrel while the one or more medication-preparation-tubing valves are in the second state, and wherein transferring the diluted medication from the syringe barrel to the infusion bag comprises transferring the diluted medication from the syringe barrel to the infusion bag while the one or more medication-preparation-tubing valves are in the first state.

16. The method according to claim 12, wherein inserting the medication port and the IV tubing port of the infusion bag into the infusion-bag receptacle such that the infusion-bag seal of the sterile closed system makes the airtight seal with the respective external surfaces of the medication port and the IV tubing port of the infusion bag comprises:

inserting the medication port and the IV tubing port of the infusion bag into the infusion-bag receptacle while the infusion-bag seal is in a non-sealing state; and thereafter, transitioning the infusion-bag seal to the sealing state, wherein transitioning the infusion-bag seal to the sealing state comprises rotating a cover of the infusion-bag seal with respect to the infusion-bag receptacle.

17. The method according to claim 12, wherein the infusion-bag receptacle is shaped so as to define an infusion-bag receptacle interior, wherein the enclosure interior and the infusion-bag receptacle interior are shaped so as to define a common wall that separates the enclosure interior and the infusion-bag receptacle interior from each other, wherein sealingly coupling the medication-port-interface needle to the medication port of the infusion bag comprises penetrating the common wall without breaking the airtight seal between the infusion-bag seal and the respective external surfaces of the medication port and the IV tubing port of the infusion bag, and wherein sealingly coupling the IV-tubing-port-interface spike to the IV tubing port of the infusion bag comprises penetrating the common wall without breaking the airtight seal between the infusion-bag seal and the respective external surfaces of the medication port and the IV tubing port of the infusion bag.

18. The method according to claim 17, wherein the common wall comprises a septum, and wherein sealingly coupling the medication-port-interface needle to the medication port of the infusion bag comprises penetrating the septum of the common wall without breaking the airtight seal between the infusion-bag seal and the respective external surfaces of the medication port and the IV tubing port of the infusion bag.

19. The method according to claim 17, wherein the common wall comprises a septum, and wherein sealingly coupling the IV-tubing-port-interface spike to the IV tubing port of the infusion bag comprises penetrating the septum of the common wall without breaking the airtight seal between the infusion-bag seal and the respective external surfaces of the medication port and the IV tubing port of the infusion bag.

20. The method according to claim 12, further comprising, before drawing the volume of IV solution from the infusion bag into the syringe barrel, sealingly coupling a syringe needle of the syringe to a septum of the syringe-interface end of the medication-preparation tubing by puncturing the syringe needle through the septum.

* * * * *